United States Patent
Zacharopoulos

(10) Patent No.: US 12,151,124 B2
(45) Date of Patent: Nov. 26, 2024

(54) X-RAY TRANSMISSION IMAGE ANALYSIS FOR THE EVALUATION OF LINAC ISOCENTER QUALITY

(71) Applicant: Aktina Corp., Congers, NY (US)

(72) Inventor: Nicholas G. Zacharopoulos, West Nyack, NY (US)

(73) Assignee: Aktina Corp., Congers, NY (US)

( * ) Notice: Subject to any disclaimer, the term of this patent is extended or adjusted under 35 U.S.C. 154(b) by 191 days.

(21) Appl. No.: 17/724,027

(22) Filed: Apr. 19, 2022

(65) Prior Publication Data

US 2022/0331608 A1 Oct. 20, 2022

Related U.S. Application Data

(60) Provisional application No. 63/176,494, filed on Apr. 19, 2021.

(51) Int. Cl.
- *A61N 5/10* (2006.01)
- *A61B 90/00* (2016.01)
- *G21K 5/08* (2006.01)

(52) U.S. Cl.
CPC ............ *A61N 5/1049* (2013.01); *A61B 90/39* (2016.02); *A61N 5/1081* (2013.01); *G21K 5/08* (2013.01); *A61B 2090/3966* (2016.02)

(58) Field of Classification Search
None
See application file for complete search history.

(56) References Cited

U.S. PATENT DOCUMENTS

| 9,192,784 B1 | 11/2015 | Ritt et al. |
| 2005/0109939 A1 | 5/2005 | Engler et al. |
| 2011/0163243 A1* | 7/2011 | Iwata ............... G21K 1/093 |
| | | 250/396 ML |

(Continued)

FOREIGN PATENT DOCUMENTS

| EP | 2186542 A1 | 5/2010 |
| EP | 2450083 B1 | 8/2013 |

(Continued)

OTHER PUBLICATIONS

Rowshanfarzad, Pejman et al., "Isocenter verification for linac-based stereotactic radiation therapy: review of principles and techniques," Journal of Applied Clinical Medical Physics, vol. 12, No. 4, 2011, pp. 185-195.

*Primary Examiner* — Marcus H Taningco
(74) *Attorney, Agent, or Firm* — Rothwell, Figg, Ernst & Manbeck, P.C.

(57) ABSTRACT

Systems and methods for determining a radiation isocenter of a linear accelerator (LINAC). Determining the radiation isocenter may include determining a set of three-dimensional (3D) radiation beam axes of the LINAC from two-dimensional (2D) radiation transmission images. The radiation isocenter may be determined based on at least the set of 3D radiation beam axes. Determining the set of 3D radiation beam axes may including constructing a 3D radiation beam axis based on a determined location of a beam axis of a radiation beam generated with a gantry of the LINAC at an angle relative to a reference gantry angle, a determined center of a shadow of a radiation opaque marker in the radiation field of the radiation beam, and the gantry angle.

30 Claims, 19 Drawing Sheets

(56) References Cited

U.S. PATENT DOCUMENTS

| | | | |
|---|---|---|---|
| 2015/0093011 A1* | 4/2015 | Gaudio | A61N 5/1075 |
| | | | 382/132 |
| 2016/0012584 A1 | 1/2016 | Gaudio | |
| 2018/0250531 A1* | 9/2018 | Ansorge | G01T 1/2914 |
| 2020/0346042 A1 | 11/2020 | Maltz | |

FOREIGN PATENT DOCUMENTS

| | | | |
|---|---|---|---|
| GB | 2589929 A | 6/2021 | |
| GB | 2602690 A | 7/2022 | |

\* cited by examiner

X-RAY TRANSMISSION IMAGE ANALYSIS FOR THE EVALUATION OF LINAC ISOCENTER QUALITY

CROSS-REFERENCE TO RELATED APPLICATION

The present application claims the benefit of priority to U.S. Provisional Patent Application Ser. No. 63/176,494, filed on Apr. 19, 2021, which is incorporated herein by reference in its entirety.

BACKGROUND

Field of Invention

The present invention relates generally to radiation therapy in which a medical linear accelerator (LINAC) delivers a radiation beam to a precise point within a patient. In particular, the present invention relates to analyzing and displaying two-dimensional x-ray transmission images for assessing the quality of a LINAC's radiation isocenter.

Discussion of the Background 1.1. LINAC Overview

Radiation therapy is a type of cancer treatment that uses beams of intense high energy radiation beams to kill cancer cells. FIGS. 1-3 illustrates a medical linear accelerator (LINAC) 100 including a gantry 102 and a couch 106. As shown in FIG. 4, the gantry 102 includes a collimator head 104 that defines a field of a radiation beam 412 generated by the LINAC 100. During treatment, the gantry 102 of the LINAC 100 delivers the radiation beams to a precise location within a patient (not shown) supported on the couch 106. To customize a radiation treatment plan, the gantry 102 may rotate about the patient, and the couch 106 may changes the patient's orientation relative a plane of rotation of the gantry 102.

As shown in FIG. 2, the gantry 102 may be capable of rotating a full 360° around the patient so as to optimize the entry of the radiation beam into the patient. As shown in FIG. 2, the gantry 102 may rotate about a gantry axis of rotation 208. As shown in FIG. 3, the couch 106 may rotate about a couch axis of rotation 310. This allows the patient's orientation to be adjusted relative to the plane of rotation of the gantry 102 so as to further optimize the entry of the radiation beam 104 into the patient.

In an ideal LINAC 100, the radiation beam would stay focused on a fixed point in space (i.e., on a tumor in the patient) as the gantry 102 rotates. Similarly, the ideal LINAC 100 would keep the tumor fixed within the radiation beam as the patient moves due to rotation of the couch 106.

As shown in FIG. 4, the LINAC 100 may have an imaging device 416 (e.g., an electronic portal imaging device (EPID)), which is used to verify the patients position before a treatment by measuring the x-ray intensity transmitted through a patient from a radiation port during a treatment session.

1.2 Radiation Isocenter

A goal of radiation therapy is to deliver the highest possible radiation dose to the tumor while minimizing the dose to the surrounding healthy tissue. To do so, radiation therapy includes the goals of (1) keeping the radiation beam precisely focused on the patient's tumor as the gantry 102 rotates and (2) keeping the patient's tumor fixed within the radiation beam as the couch 106 rotates. These two goals, however, are rarely perfectly realized. The gantry 102 commonly flexes under its own weight, effectively blurring the radiation beam. The rotation of the couch 106 also is often not perfectly circular and/or the axis of rotation 310 of the couch 106 commonly does not intersect the axis of rotation 208 of the gantry 102.

To minimize the effect of these common LINAC imperfections, the tumor should be placed at a point in space that minimizes the maximum beam-to-target error. This location is referred to as the isocenter.

1.3 Isocenter Size

The maximum beam axis miss distance for all combinations of gantry and couch rotation is the isocenter size. A smaller isocenter will result in a more accurate treatment.

1.4 Existing Method

An existing method for analyzing isocenter includes two main steps: (1) measure EPID x-ray transmission images of a radiation-opaque marker positioned at (or near) isocenter with different gantry and couch rotations and (2) analyze the images to determine the size of the isocenter.

The setup shown in FIG. 4 is typically used to accomplish the first step. In FIG. 4, the LINAC 100 is delivering a radiation beam 412 through a radiation opaque marker 414 that is placed at isocenter. The imaging device 416 acquires a two-dimensional transmission image of the radiation beam 412 as it passes through the marker 414.

A detailed view of a marker assembly 500 including the radiation opaque marker 414 is shown in FIG. 5. In FIG. 5, a high density spherical marker 414 is connected to a low density support rod 502 that then connects to a base 504. The base 504 is set on a top of the couch 106 so that the marker 414 can be positioned at (or near) isocenter.

FIG. 6 shows a typical image 600 (e.g., an EPID image) through the marker 414. In FIG. 6, the dark square region 602 is created by a square radiation field of the radiation beam 412 exposing the imaging device 410, and the lighter inner circular shape 604 is created by the shadow of the radiation opaque marker 414 that is located within the radiation field.

The existing method for measuring the isocenter involves rotating the gantry 102 through a set of fixed gantry angles while the couch 106 remains at 0° and acquiring an EPID image for each gantry position. Additional EPID images are acquired while the gantry 102 remains fixed at 0° and the couch 106 rotates through a set of fixed couch angles.

The second step of the existing method includes analyzing the images described above to determine the size of isocenter. This step can be further broken down into two subprocesses: (2a) using image processing techniques to find the centers of the field and the marker 414 in each image (an example of an image 700 with the determined field and marker locations is shown in FIG. 7) and (2b) computing the largest marker center to field center distance for all images acquired and assigning this largest value to the isocenter size.

SUMMARY

The existing use of the field-to-marker distances for all EPID images acquired to analyze isocenter models a complex three-dimensional process with a two-dimensional coordinate system (CS). The existing method maintains the data, which is acquired from an EPID image, in the two-dimensional image CS. By doing so, it is often difficult to intuitively understand the nature of problems when they arise with the LINAC isocenter. Aspects of the invention may overcome one or more of the problems with the existing method (e.g., by replacing and improving upon sub-process step 2b of the existing method).

Aspects of the invention may include (1) using a linear accelerator (LINAC) to acquire radiation transmission images of a radiation-opaque marker positioned at (or near) isocenter with different gantry and/or couch rotations and (2) analyzing the images to determine the size of the isocenter, a marker placement error (i.e., the isocenter position relative to the current marker position), and/or the couch walkout. Analyzing the images may include finding the centers of the radiation field and the marker in the images.

With respect to determining isocenter size, instead of comparing the field and marker centers to find the largest difference and assigning the largest distance as the isocenter size, the the field and marker centers may be transformed from the two-dimensional (2D) image coordinate system (CS) into a three-dimensional (3D) (e.g., real-world) CS. Moving from a 2D image CS to a 3D CS may provide the advantage of allowing for a more flexible analysis and intuitive display in 3D that more accurately reflects the underlying processes.

In some aspects, in analyzing the images to characterize the LINAC's isocenter, gantry and couch rotations may be treated differently. When the gantry rotates, the field moves but the marker does not. Similarly, when the couch rotates, the marker moves but the field remains still. In some aspects, therefore, images may be grouped into two categories: (1) images for isocenter determination and/or marker placement error determination, which may be acquired with gantry rotations while the couch remains at a fixed couch angle (e.g., 0°), and (2) images for couch walkout determination, which may be acquired with couch rotations while the gantry remains at a fixed gantry angle (e.g., 0°).

One aspect of the invention may provide a method including determining a set of three-dimensional (3D) radiation beam axes of a linear accelerator (LINAC) from two-dimensional (2D) radiation transmission images, wherein the set of 3D radiation beam axes includes at least first and second 3D radiation beam axes. The method may include determining a radiation isocenter of the LINAC based on at least the set of 3D radiation beam axes.

In some aspects, determining the first 3D radiation beam axis may include positioning a gantry of the LINAC at a first gantry angle relative to a reference gantry angle, and positioning the gantry may include rotating the gantry about a gantry axis of rotation. In some aspects, determining the first 3D radiation beam axis may include, with the gantry positioned at the first gantry angle, using the LINAC to generate a first radiation beam. In some aspects, determining the first 3D radiation beam axis may include, with the gantry positioned at the first gantry angle, using an imaging device of the LINAC to acquire a first two-dimensional (2D) radiation transmission image indicative of a radiation field of the first radiation beam after passing by a radiation opaque marker. In some aspects, determining the first 3D radiation beam axis may include determining a location of a beam axis of the first radiation beam and a center of a shadow of the radiation opaque marker in the radiation field of the first radiation beam based on the first 2D radiation transmission image. In some aspects, determining the first 3D radiation beam axis may include constructing the first 3D radiation beam axis based on the determined location of the beam axis of the first radiation beam, the determined center of the shadow of the radiation opaque marker in the radiation field of the first radiation beam, and the first gantry angle.

In some aspects, constructing the first 3D radiation beam axis may include rotating the first 2D radiation transmission image about a first image rotation axis that is coincident with the determined center of the shadow of the radiation opaque marker in the radiation field of the first radiation beam and parallel with the gantry axis of rotation. In some aspects, the first 2D radiation transmission image may be rotated in an amount equal to the first gantry angle. In some aspects, the first 3D radiation beam axis may be coincident with the determined location of the beam axis of the first radiation beam in the rotated first 2D radiation transmission image and perpendicular to a plane of the rotated first 2D radiation transmission image.

In some alternative aspects, constructing the first 3D radiation beam axis may include generating an initial 3D radiation beam axis that is coincident with the determined location of the beam axis of the first radiation beam in the first 2D radiation transmission image and perpendicular to a plane of the first 2D radiation transmission image and rotating the initial 3D radiation beam axis about a first image rotation axis that is coincident with the determined center of the shadow of the radiation opaque marker in the radiation field of the first radiation beam and parallel with the gantry axis of rotation, and the initial 3D radiation beam axis may be rotated in an amount equal to the first gantry angle.

In some aspects, determining the second 3D radiation beam axis may include positioning the gantry of the LINAC at a second gantry angle relative to the reference gantry angle. In some aspects, determining the second 3D radiation beam axis may include, with the gantry positioned at the second gantry angle, using the LINAC to generate a second radiation beam. In some aspects, determining the second 3D radiation beam axis may include, with the gantry positioned at the second gantry angle, using the imaging device of the LINAC to acquire a second 2D radiation transmission image indicative of a radiation field of the second radiation beam after passing by the radiation opaque marker. In some aspects, determining the second 3D radiation beam axis may include determining a location of a beam axis of the second radiation beam and a center of a shadow of the radiation opaque marker in the radiation field of the second radiation beam based on the second 2D radiation transmission image. In some aspects, determining the second 3D radiation beam axis may include constructing the second 3D radiation beam axis based on the determined location of the beam axis of the second radiation beam, the determined center of the shadow of the radiation opaque marker in the radiation field of the second radiation beam, and the second gantry angle.

In some aspects, constructing the second 3D radiation beam axis may include rotating the second 2D radiation transmission image about a second image rotation axis that is coincident with the determined center of the shadow of the radiation opaque marker in the radiation field of the second radiation beam and parallel with the gantry axis of rotation. In some aspects, the second 2D radiation transmission image may be rotated in an amount equal to the second gantry angle. In some aspects, the second 3D radiation beam axis may be coincident with the determined location of the beam axis of the second radiation beam in the rotated second 2D radiation transmission image and perpendicular to a plane of the rotated second 2D radiation transmission image.

In some alternative aspects, constructing the second 3D radiation beam axis may include generating an initial second 3D radiation beam axis that is coincident with the determined location of the beam axis of the second radiation beam in the second 2D radiation transmission image and perpendicular to a plane of the second 2D radiation transmission image and rotating the initial second 3D radiation beam axis about a second image rotation axis that is coincident with the determined center of the shadow of the radiation opaque marker in the radiation field of the second radiation beam and parallel with the gantry axis of rotation, and the initial second 3D radiation beam axis may be rotated in an amount equal to the second gantry angle.

In some aspects, a couch may be positioned at a fixed couch angle while the LINAC is used to generate the first and second radiation beams and the imaging device of the LINAC is used to acquire the first and second 2D radiation transmission images.

In some aspects, determining the radiation isocenter may include, for each 3D radiation beam axis of the set of 3D radiation beam axes, determining a beam axis miss distance between a location in 3D space and the 3D radiation beam axis. In some aspects, determining the radiation isocenter may include determining which of the beam axis miss distances determined for the 3D radiation beam axes of the set of 3D radiation beam axes is the greatest, and the greatest of the beam axis miss distances determined for the 3D radiation beam axes of the set of 3D radiation beam axes may be a maximum beam axis miss distance for the location. In some aspects, determining the radiation isocenter may include finding a location in 3D space that has the smallest maximum beam axis miss distance. In some aspects, the beam axis miss distance between the location in 3D space and the 3D radiation beam axis may be the shortest distance between the location and the 3D radiation beam axis. In some aspects, a size of the radiation isocenter may be the maximum beam axis miss distance for the location.

In some aspects, the method may further include positioning a tumor at the determined radiation isocenter.

In some aspects, the method may further include determining a marker movement vector for each couch angle of a set of couch angles, and the set of couch angles may include at least a first couch angle relative to a reference couch angle and a second couch angle relative to the reference couch angle. In some aspects, the method may further include determining a marker to 3D radiation beam axis error distance for each combination of a couch angle of the set of couch angles and a 3D radiation beam axis of the set of 3D radiation beam axes based on the determined marker movement vectors, and the marker to 3D radiation beam axis error distance may represent the shortest distance between a location of a radiation opaque marker and the 3D radiation beam axis error.

In some aspects, determining the marker movement vector for the first couch angle may include, with a couch of the LINAC positioned at the reference couch angle and a gantry of the LINAC positioned at a reference gantry angle, using the LINAC to generate a first reference radiation beam. In some aspects, determining the marker movement vector for the first couch angle may include, with the couch positioned at the reference couch angle and the gantry positioned at the reference gantry angle, using an imaging device of the LINAC to acquire a reference couch angle two-dimensional (2D) radiation transmission image indicative of a radiation field of the first reference radiation beam after passing by the radiation opaque marker. In some aspects, determining the marker movement vector for the first couch angle may include determining a center of a shadow of the radiation opaque marker in the radiation field of the first reference radiation beam based on the reference couch angle 2D radiation transmission image. In some aspects, determining the marker movement vector for the first couch angle may include positioning the couch at the first couch angle. In some aspects, determining the marker movement vector for the first couch angle may include, with the couch positioned at the first couch angle and the gantry positioned at the reference gantry angle, using the LINAC to generate a second reference radiation beam. In some aspects, determining the marker movement vector for the first couch angle may include, with the couch positioned at the first couch angle and the gantry positioned at the reference gantry angle, using the imaging device of the LINAC to acquire a first couch angle 2D radiation transmission image indicative of a radiation field of the second reference radiation beam after passing by the radiation opaque marker. In some aspects, determining the marker movement vector for the first couch angle may include determining a center of a shadow of the radiation opaque marker in the radiation field of the second reference radiation beam based on the first couch angle 2D radiation transmission image. In some aspects, determining the marker movement vector for the first couch angle may include determining the marker movement vector for the first couch angle based on a comparison of the center of the shadow of the radiation opaque marker in the radiation field of the first reference radiation beam with the center of the shadow of the radiation opaque marker in the radiation field of the second reference radiation beam.

In some aspects, determining the marker movement vector for the second couch angle may include positioning the couch at the second couch angle. In some aspects, determining the marker movement vector for the second couch angle may include, with the couch positioned at the second couch angle and the gantry positioned at the reference gantry angle, using the LINAC to generate a third reference radiation beam. In some aspects, determining the marker movement vector for the second couch angle may include, with the couch positioned at the second couch angle and the gantry positioned at the reference gantry angle, using the imaging device of the LINAC to acquire a second couch angle 2D radiation transmission image indicative of a radiation field of the third reference radiation beam after passing by the radiation opaque marker. In some aspects, determining the marker movement vector for the second couch angle may include determining a center of a shadow of the radiation opaque marker in the radiation field of the third reference radiation beam based on the second couch angle 2D radiation transmission image. In some aspects, determining the marker movement vector for the second couch angle may include determining the marker movement vector for the second couch angle based on a comparison of the center of the shadow of the radiation opaque marker in the radiation field of the first reference radiation beam with the center of the shadow of the radiation opaque marker in the radiation field of the third reference radiation beam.

In some aspects, the method may further include determining a clinical isocenter, wherein determining the clinical isocenter comprises determining a location in space that minimizes a maximum marker to beam axis error distance. In some aspects, determining the location in space that minimizes the maximum marker to 3D radiation beam axis error distance may include predicting a couch axis of rotation based on shadows of the radiation opaque marker at different couch angles. In some aspects, determining the location in space that minimizes the maximum marker to 3D radiation beam axis error distance may include predicting a set of positions of the radiation opaque marker at a new reference position displaced by couch rotation about the predicted couch axis of rotation. In some aspects, determining the location in space that minimizes the maximum marker to beam axis error distance may include determining a predicted marker to 3D radiation beam axis error distance for each combination of a couch angle of the set of couch angles and a 3D radiation beam axis of the set of 3D radiation beam axes based on the determined marker movement vectors, and the predicted marker to 3D radiation beam axis error distance may represent the shortest distance between a location of a radiation opaque marker and the 3D radiation beam axis error. In some aspects, determining the location in space that minimizes the maximum marker to beam axis error distance may include determining a reference marker position that minimizes the maximum marker to beam axis error distance. In some aspects, the method may further include placing a tumor at the determined clinical isocenter.

Another aspect of the invention may provide an apparatus configured to determine a set of three-dimensional (3D) radiation beam axes of a linear accelerator (LINAC) from two-dimensional (2D) radiation transmission images, and the set of 3D radiation beam axes may include at least first and second 3D radiation beam axes. The apparatus may be configured to determine a radiation isocenter of the LINAC based on at least the set of 3D radiation beam axes.

Still another aspect of the invention may provide a method including determining a marker movement vector for each couch angle of a set of couch angles of a linear accelerator (LINAC), and the set of couch angles may include at least a first couch angle relative to a reference couch angle and a second couch angle relative to the reference couch angle. The method may include determining a marker to 3D radiation beam axis error distance for each combination of a couch angle of the set of couch angles and a 3D radiation beam axis of a set of 3D radiation beam axes based on the determined marker movement vectors, and the marker to 3D radiation beam axis error distance may represent the shortest distance between a location of a radiation opaque marker and the 3D radiation beam axis error.

In some aspects, the method may further include placing a tumor at a location determined based on the determined marker to 3D radiation beam axis error distance for each combination of a couch angle of the set of couch angles and a 3D radiation beam axis of a set of 3D radiation beam axes.

Yet another aspect of the invention may provide an apparatus configured to determine a marker movement vector for each couch angle of a set of couch angles of a linear accelerator (LINAC), and the set of couch angles may include at least a first couch angle relative to a reference couch angle and a second couch angle relative to the reference couch angle. The apparatus may be configured to determine a marker to 3D radiation beam axis error distance for each combination of a couch angle of the set of couch angles and a 3D radiation beam axis of a set of 3D radiation beam axes based on the determined marker movement vectors, and the marker to 3D radiation beam axis error distance may represent the shortest distance between a location of a radiation opaque marker and the 3D radiation beam axis error.

Still another aspect of the invention may provide a computer program including instructions for adapting an apparatus to perform any of the methods set forth above. Yet another aspect of the invention may provide a carrier containing the computer program, and the carrier may be one of an electronic signal, optical signal, radio signal, or compute readable storage medium.

Still another aspect of the invention may provide an apparatus including processing circuitry and a memory. The memory may contain instructions executable by the processing circuitry, whereby the apparatus is operative to perform any of the methods set forth above.

Yet another aspect of the invention may provide an apparatus adapted to any of the methods set forth above.

Still another aspect of the invention may provide any combination of the aspects set forth above.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

DETAILED DESCRIPTION OF PREFERRED EMBODIMENTS

Figure 1:
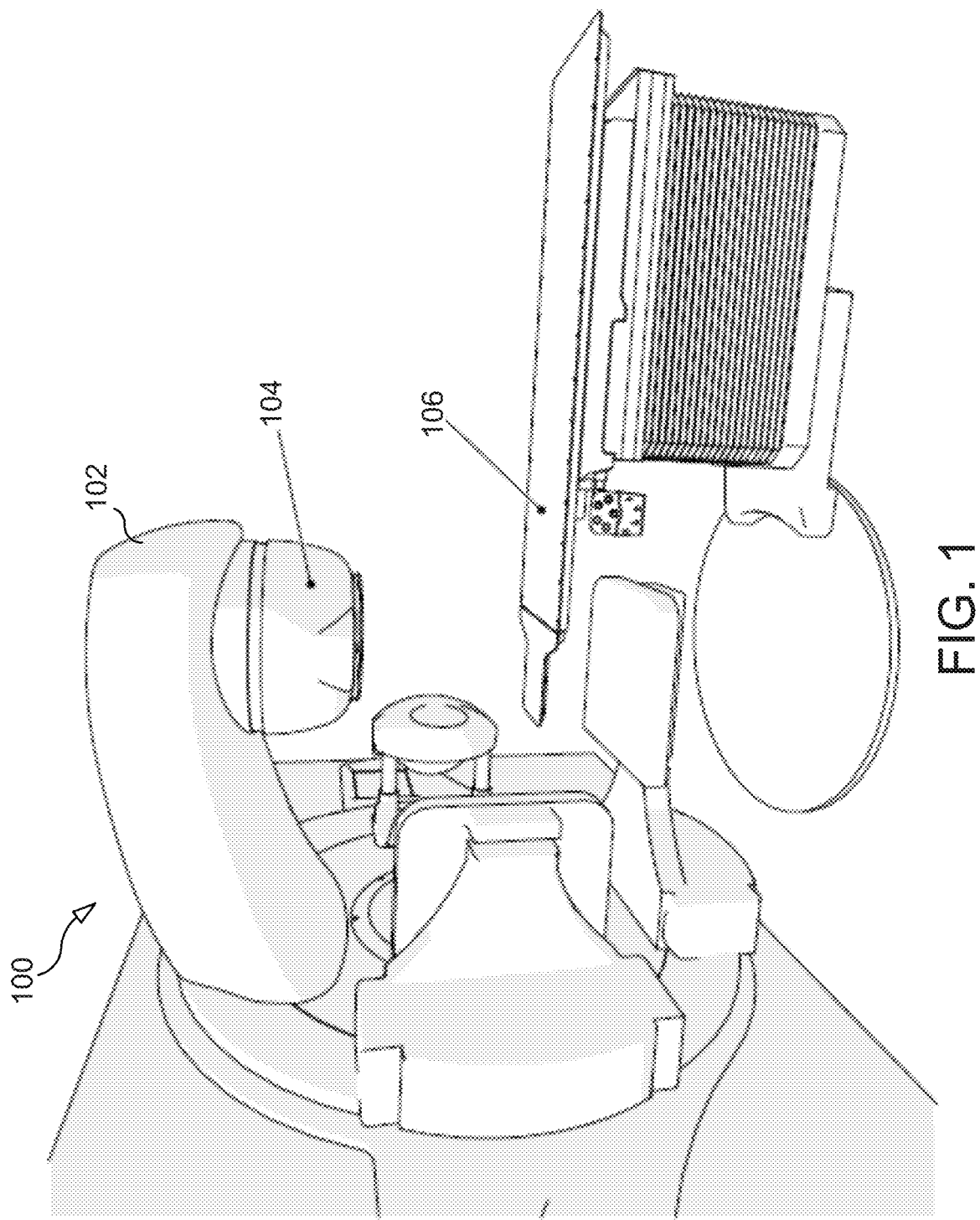
FIG. 1 illustrates a medical linear accelerator (LINAC).
Figure 2:
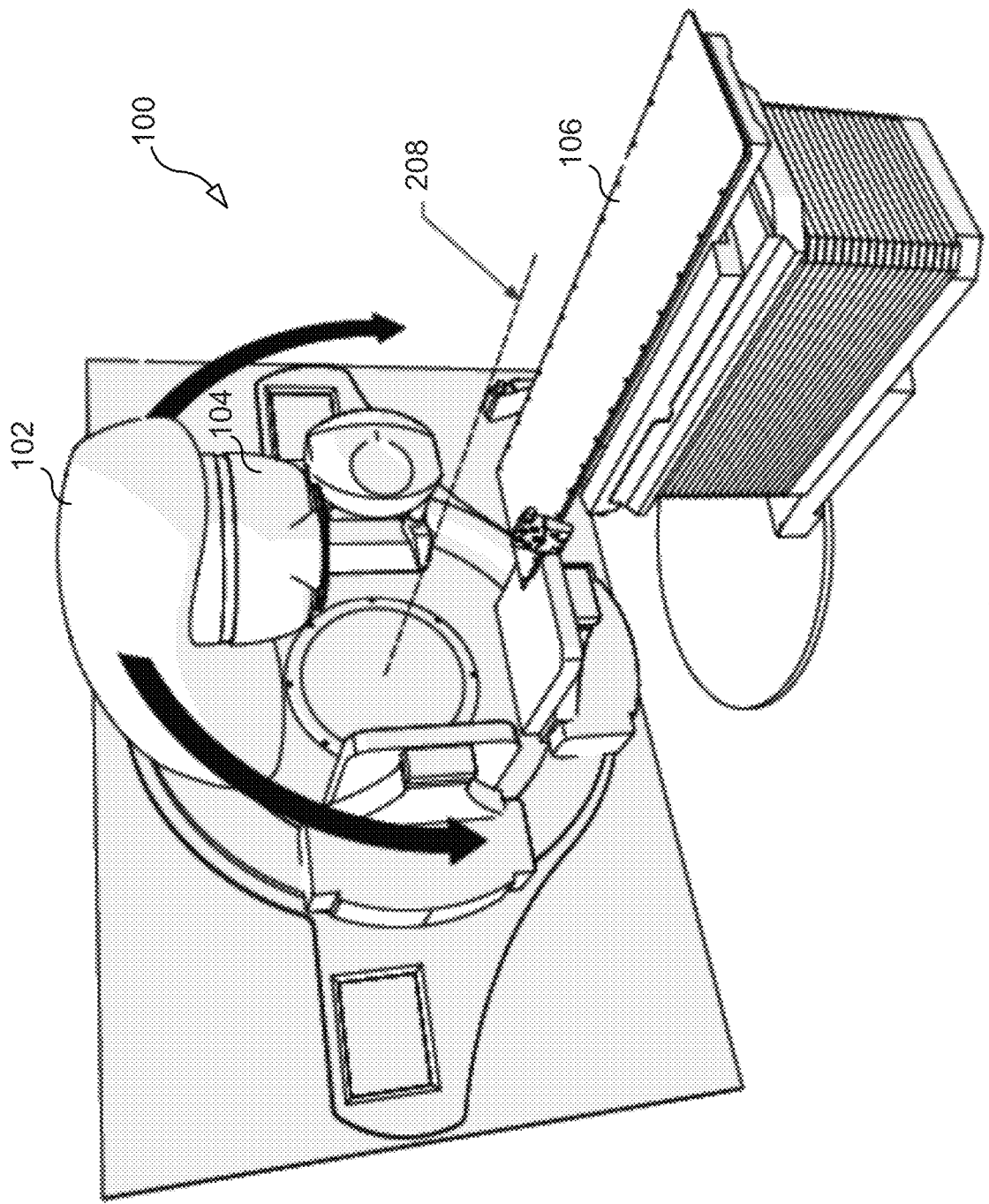
FIG. 2 illustrates rotation of a gantry of the LINAC.
Figure 3:
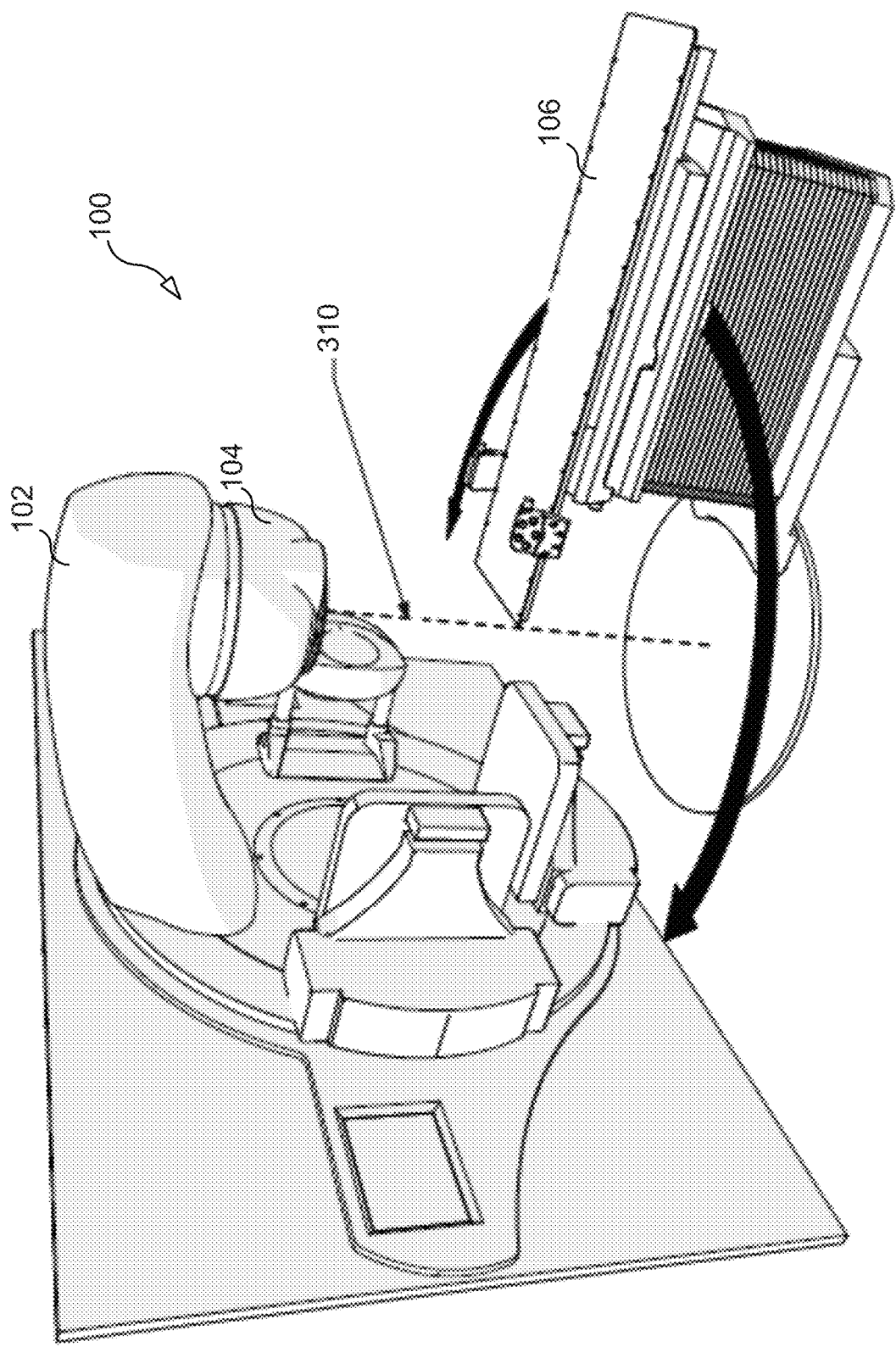
FIG. 3 illustrates rotation of a couch of the LINAC.
Figure 4:
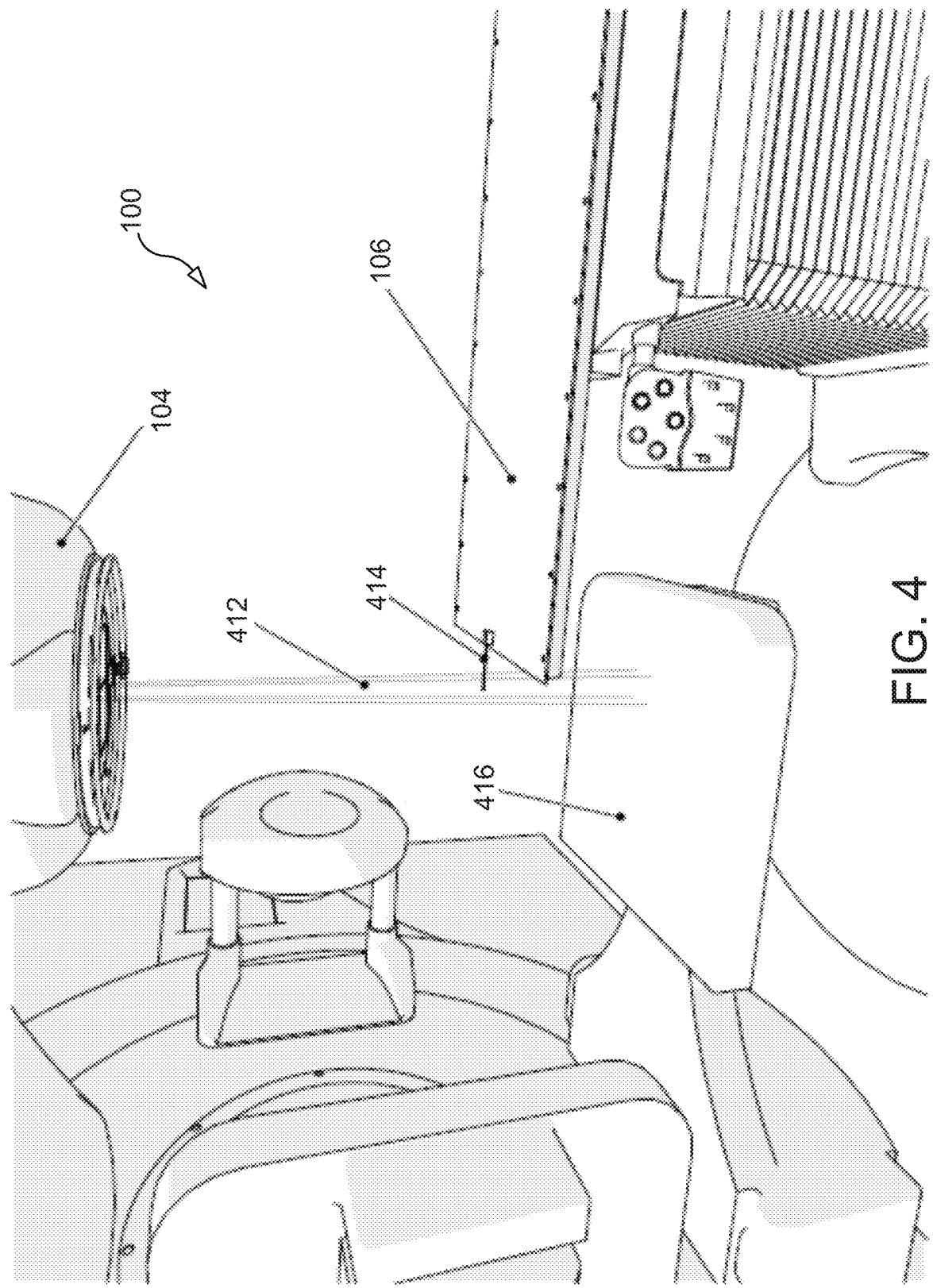
FIG. 4 illustrates a radiation beam and imaging panel of the LINAC.
Figure 5:
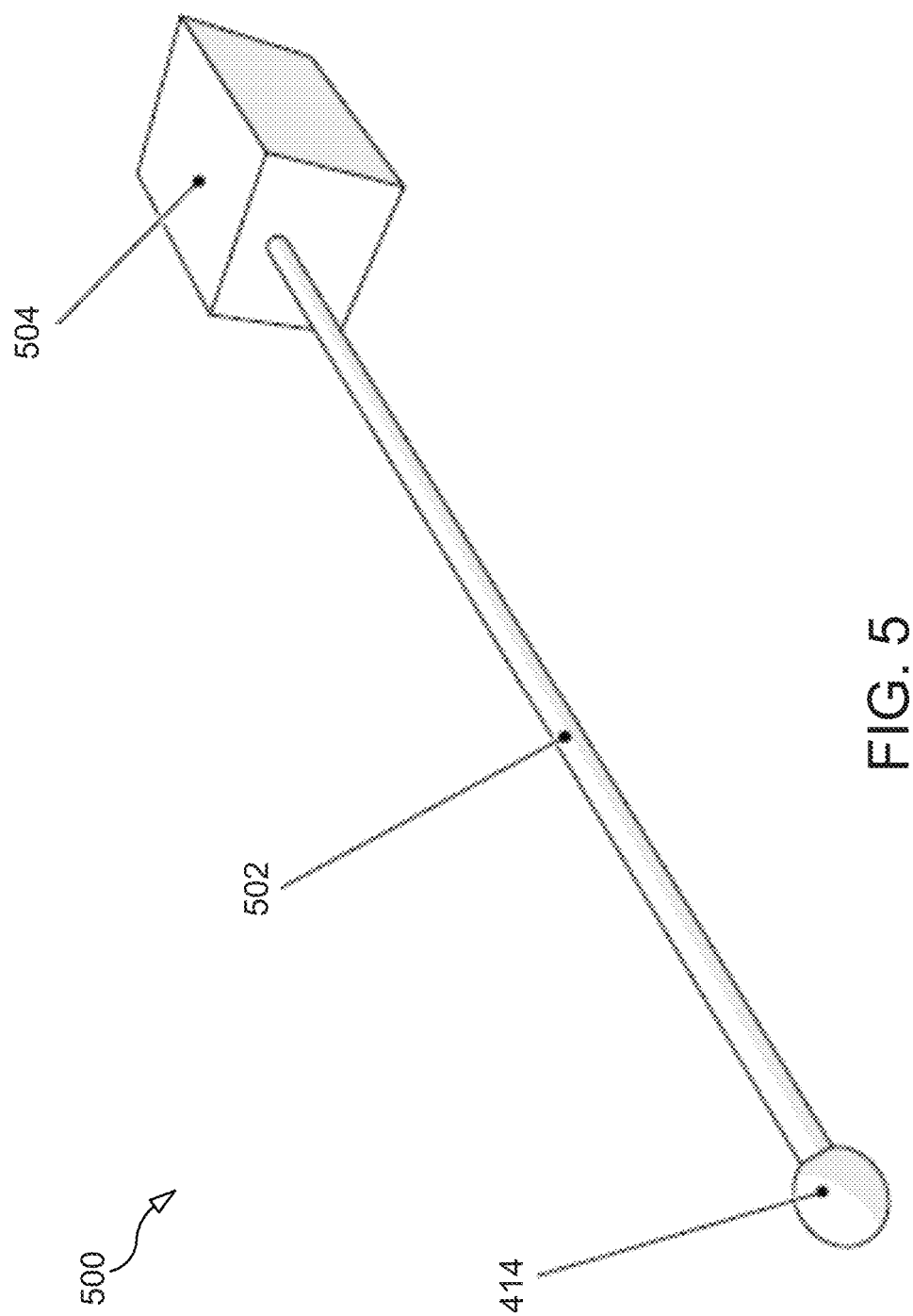
FIG. 5 illustrates a marker assembly according to some aspects.

In this application, the term "beam axis" can be a three-dimensional vector that represents the center of a radiation beam.

In this application, the term "beam-axis miss distance" can be the shortest distance between a target (e.g., the center of a tumor) and any point along the beam axis.

In this application, the term "CS" or "Coordinate System" can be, for example, a two-dimensional (2D) CS, such as a CS of an image (e.g., an EPID image), or three-dimensional (3D) CS, such as the 3D CS of a linear accelerator (LINAC) (e.g., LINAC 100).

In this application, the term "couch walkout" can be the amount a patient's tumor, if positioned at (or near) isocenter, moves when the couch 106 rotates through its full range of motion.

In this application, the term "couch" can be a component (e.g., couch 106) of a LINAC (e.g., LINAC 100) that supports the patient.

In this application, the term "imaging device" (e.g., an electronic portal imaging device (EPID) can be a component (e.g., imaging device 416) of a LINAC (e.g., LINAC 100) that measures the x-ray intensity transmitted through a patient from a radiation port (e.g., during a treatment session). The imaging device may, for example, convert electronically a radiation signal into a two-dimensional (2D) digital radiographic image to verify the correct beam placement in relation to the patient's anatomy.

In this application, the term "gantry" may be a component (e.g., gantry 102) of a LINAC (e.g., LINAC 100) that rotates about the patient while delivering the radiation beam.

In this application, the term "isocenter" can be the location in space that minimizes the radiation beam axis miss distance for all gantry angles.

In this application, the term "marker placement error" can be the three-dimensional vector between the real LINAC isocenter location and the placed location of the marker when acquiring EPID images for analyzing isocenter.

In some aspects, the LINAC 100 may (1) acquire radiation transmission images of a radiation-opaque marker 414 positioned at (or near) isocenter with different gantry and/or couch rotations and (2) analyze the images to determine the size of the isocenter, a marker placement error (i.e., the isocenter position relative to the current marker position), and/or the couch walkout. Analyzing the images may include finding the centers of the radiation field and the marker in the images.

2.1 Isocenter

Figure 6:
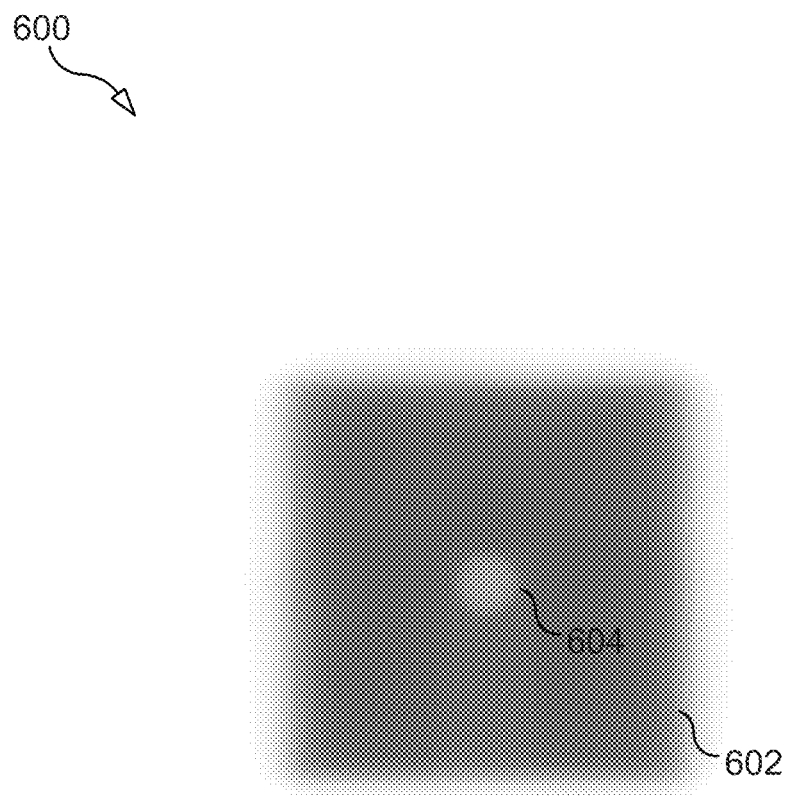
FIG. 6 illustrates an unprocessed radiation transmission image according to some aspects.
Figure 7:
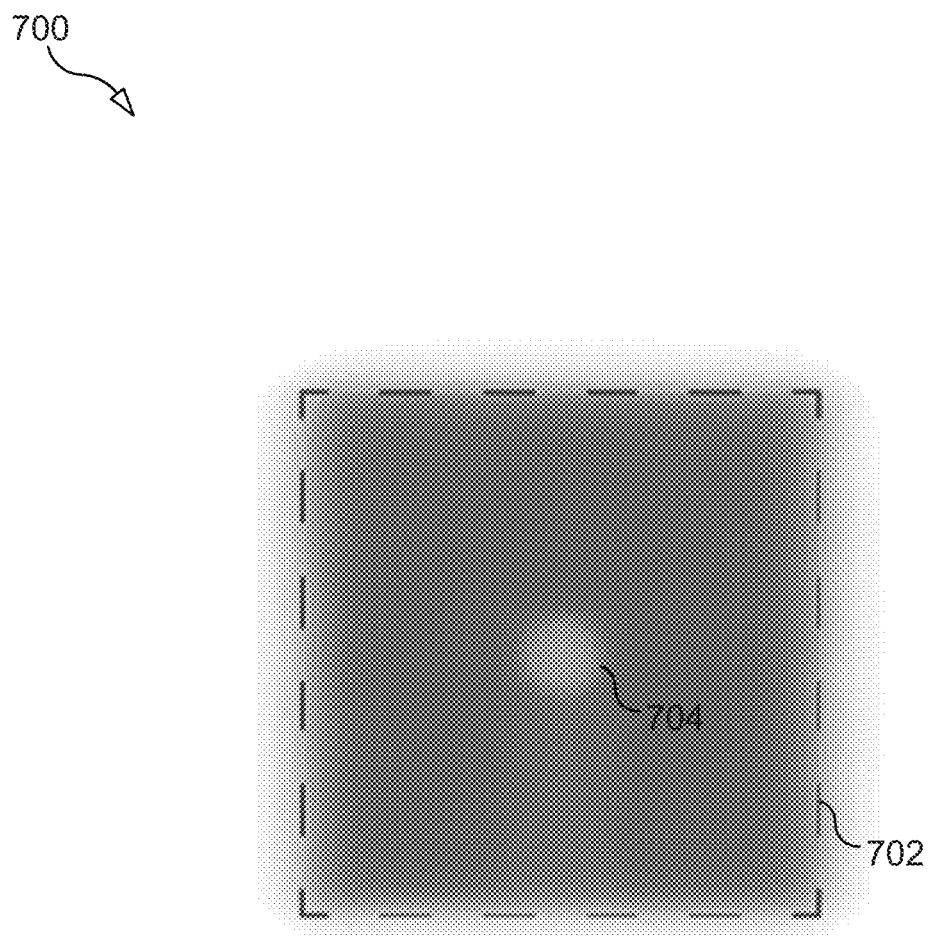
FIG. 7 illustrates a processed radiation transmission image according to some aspects.
Figure 8:
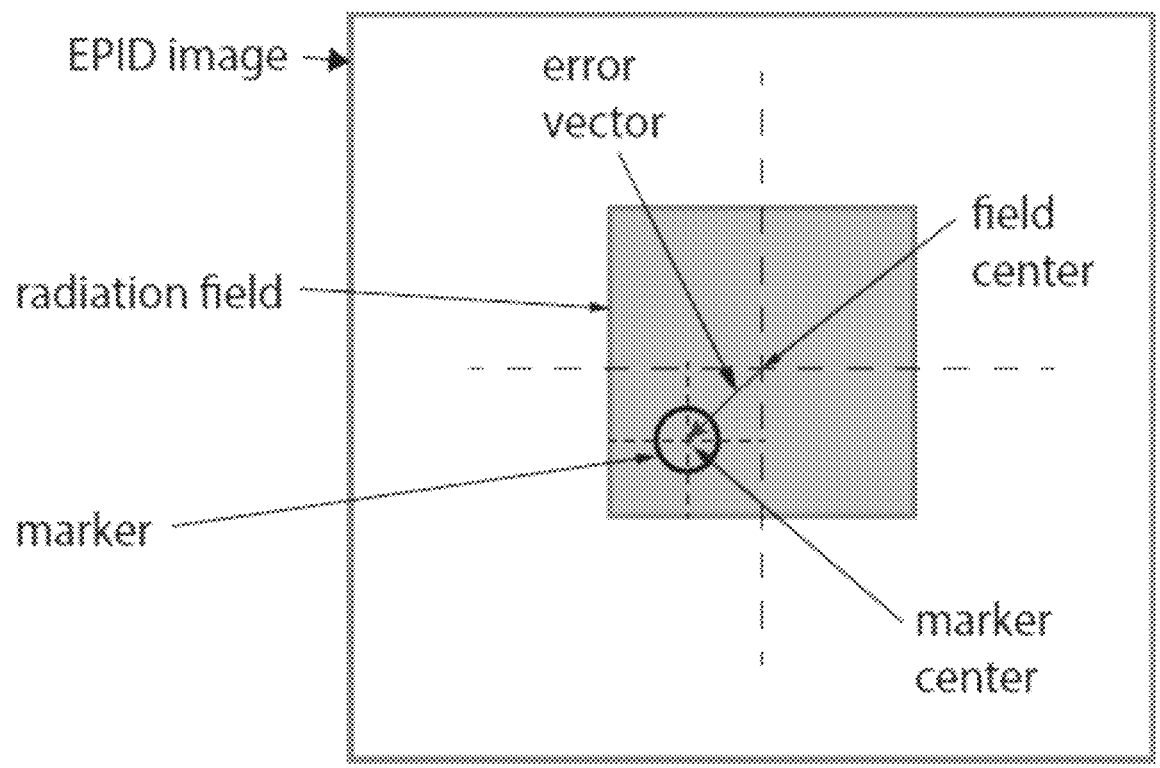
FIG. 8 illustrates a difference in the positions of a radiation opaque marker and radiation field centers according to some aspects.
Figure 9:
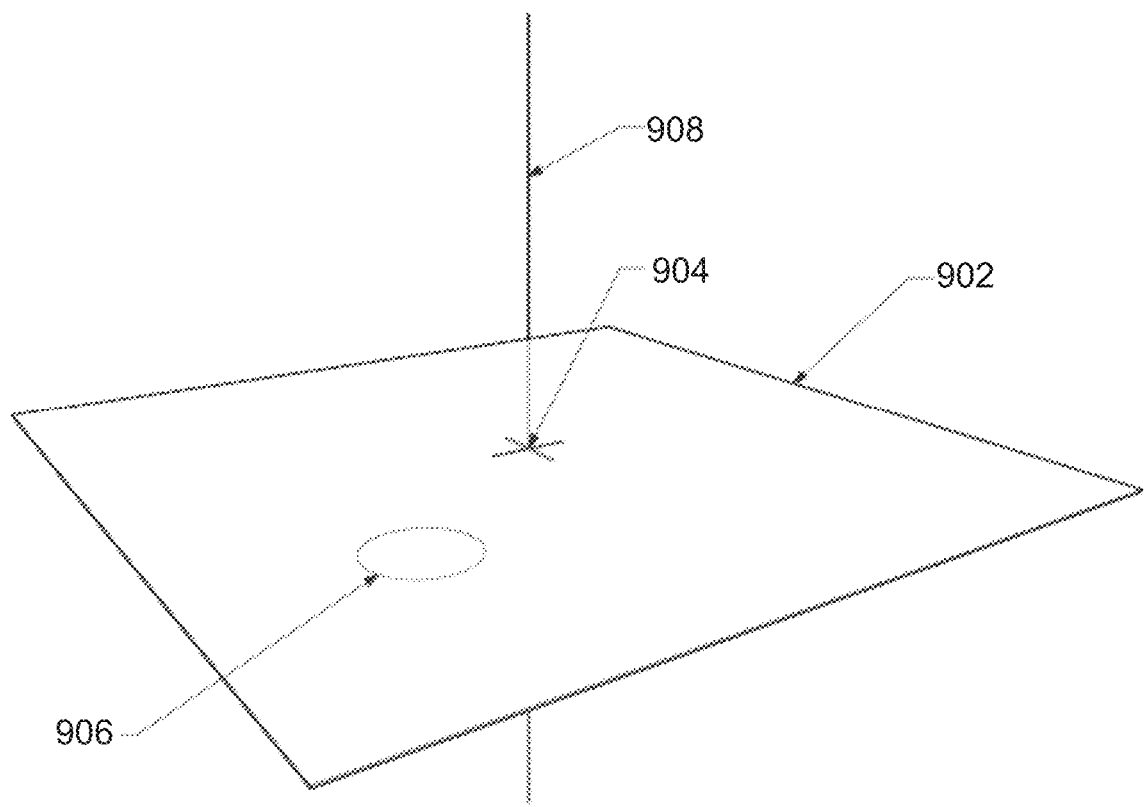
FIG. 9 illustrates a processed two-dimensional image showing the found radiation field, the center of the radiation field, the found shadow of the marker, and the radiation field central axis according to some aspects.
Figure 10:
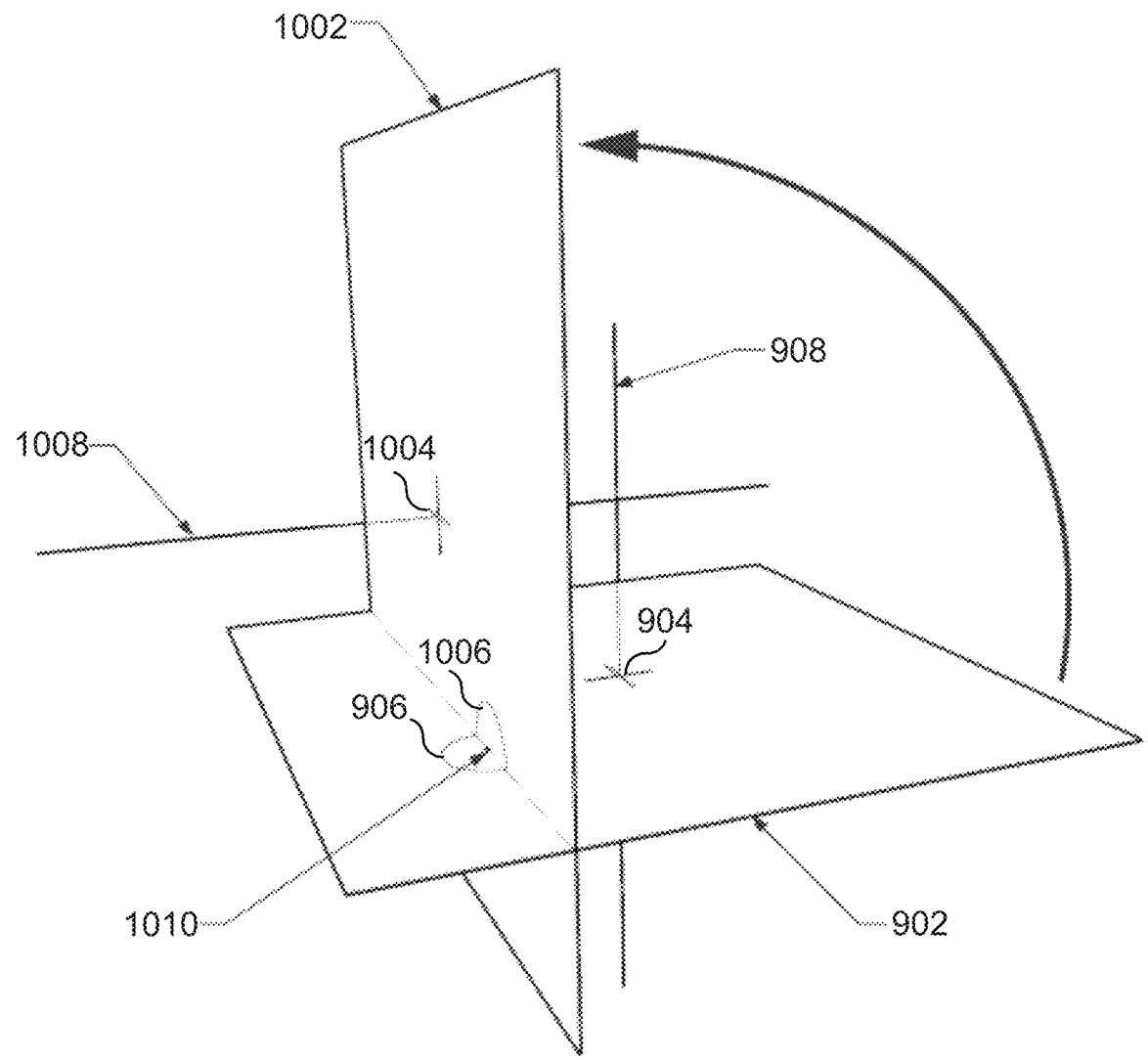
FIG. 10 illustrates rotation of the original two-dimensional image about the center of the shadow of the marker to a new location by an amount and direction corresponding to an amount and direction of gantry rotation at the time of image acquisition according to some aspects.

In some aspects, determining isocenter may involve analyzing images (e.g., EPID images) where the couch 106 remains at a fixed couch angle (e.g., 0°) while the gantry angle is varied (e.g., through its full range of motion). In some aspects, determining isocenter may involve analyzing only images where the couch 106 remains at the fixed couch angle while the gantry angle is varied. Some aspects may include determining locations of the beam axes of the radiation beams in the images and finding the centers of the marker 414 in the images (see, e.g., FIGS. 6-8). As shown in FIGS. 9 and 10, some aspects may include transforming the beam axis locations and marker centers from the two-dimensional (2D) image coordinate system (CS) into a three-dimensional (3D) CS. In some aspects, as shown in FIGS. 9 and 10, because the gantry 102 rotates while the marker 414 remains fixed in space, the transformation from the 2D image CS to the 3D (e.g., real-world) CS may use the shadow 906 of the marker 414 as a fixed reference point (e.g. all beam axis determinations will be relative to the marker location, which is a fixed point in space).

In some aspects, as shown in FIG. 9, characterizing the isocenter may include, for each image acquired by an imaging device 416 (e.g., EPID) of the LINAC 100 while the gantry 102 rotates and the couch angle remains fixed, using image processing techniques to (i) determine a location of a beam axis 908 of a radiation beam 412 generated using a gantry 102 of the LINAC 100 and (ii) find a center of a shadow 906 of a marker 414 in a radiation field 902 of the radiation beam 412. In some aspects, determining the location of the beam axis 908 may include finding a center 904 of a radiation field 902 of a radiation beam 412 generated using a gantry 102 of the LINAC 100. In some alternative aspects, determining the location of the beam axis 908 may include finding an average of centers 904 of radiation fields 412 generated using a gantry 102 of the LINAC 100 at (i) a first collimator angle and (ii) a second collimator angle that is 180 degrees different that the first collimator angle (e.g., to account for errors if the radiation field is not well calibrated).

In some aspects, as shown in FIG. 10, characterizing the isocenter may include, for each image acquired by the imaging device 416 while the gantry 102 rotates and the couch angle remains fixed, constructing a beam axis 908 that is coincident with the determined location of the beam axis 908 in the image and perpendicular to the imaging plane. Some aspects may include, as shown in FIG. 10, for each image acquired by the imaging device 416 while the gantry 102 rotates and the couch angle remains fixed (other than an image acquired with a gantry angle of 0° for which no rotation would be needed), rotating the constructed beam axis 908 about the center 1010 of the shadow 906 of the marker 414 to a new position by an amount and direction equal to the gantry rotation that was used when the image was acquired. Some alternative aspects may include, as shown in FIG. 10, for each image acquired by the imaging device 416 while the gantry 102 rotates and the couch angle remains fixed (other than an image acquired with a gantry angle of 0° for which no rotation would be needed), rotating the first 2D radiation transmission image about a first image rotation axis that is coincident with the determined center of the shadow of the radiation opaque marker in the radiation field of the first radiation beam and parallel with the gantry axis of rotation, the first 2D radiation transmission image may be rotated in an amount equal to the gantry angle of rotation, and the first 3D radiation beam axis may be coincident with the determined location of the beam axis of the first radiation beam in the rotated first 2D radiation transmission image and perpendicular to a plane of the rotated first 2D radiation transmission image. FIG. 10 shows the rotated radiation field 1002, the center 1004 of the rotated radiation field 1002, the shadow 1006 of the marker 414 in the rotated radiation field 1002, and the rotated beam axis 1008 according to some aspects.

Figure 11:
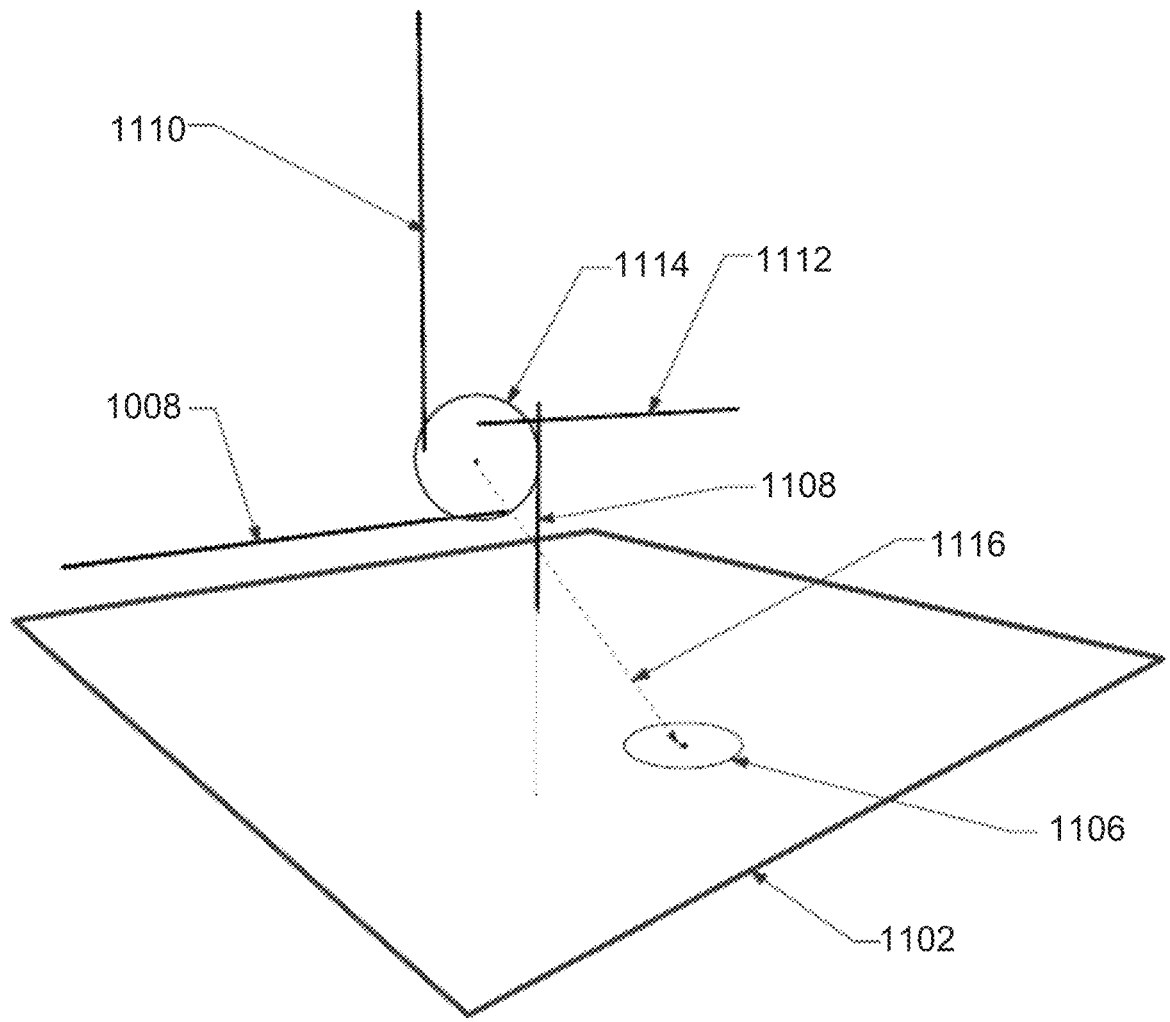
FIG. 11 illustrates the superposition of beam axes that have been transformed from two-dimensional image coordinates into three-dimensional, real-world coordinates and define an isocenter according to some aspects.

In some aspects, as shown in FIG. 11, rotating the constructed beam axes in an amount equal to the angle of gantry rotation (or rotating image by an amount equal to the angle of gantry rotation and using the rotated images to construct beam axes) may create a set of three-dimensional beam axes (e.g., including rotated beam axes 1008, 1110, and 1112 and the constructed beam axis 1108 at a gantry rotation angle of 0°) with a common shadow 1106 of the marker 414 in the radiation field 1102 of the radiation beam 412 with the gantry 102 at a gantry rotation angle of 0° (and a couch 106 at the fixed couch angle) as a reference point (e.g., for calculation of the isocenter 1114). Some aspects may include using the three-dimensional beam axes (e.g., including 3D beam axes 1008, 1108, 1110, and 1112) to calculate the isocenter 1114. Some aspects may include calculating the isocenter 1114 by finding the point in space that minimizes the maximum beam-axis miss distance between that point and all of the three-dimensional beam axes. Some aspects may include determining the size of the isocenter as the largest miss distance between the center of the isocenter 1114 and all of the three-dimensional beam axes considered.

2.2 Marker Placement Error

In some aspects, the three-dimensional isocenter analysis described in section 2.1 above may have the extra benefit of decoupling any marker placement error from the resulting isocenter size. For example, as shown in FIG. 11, the marker positioning error may be determined as the vector 1116 from (a) the center of the shadow 1106 of the marker 414 in the radiation field 1102 of the radiation beam 412 with the gantry 102 at a gantry rotation angle of 0° (and a couch 106 at the fixed couch angle) to (b) the location of the found isocenter 1114.

2.3 Couch Walkout

Some aspects may include performing a couch walkout determination to determine how much a tumor placed at the isocenter 1114 would move when the couch 106 rotates. In some aspects, in contrast to an isocenter determination in which the marker 414 remains fixed and the radiation field varies as the gantry 102 is rotated, the LINAC 100 may make couch walkout measurements with a fixed radiation field (e.g., with the gantry 102 positioned at a fixed gantry angle) and marker 414 that (potentially) moves as the couch 106 is rotated.

Figure 12:
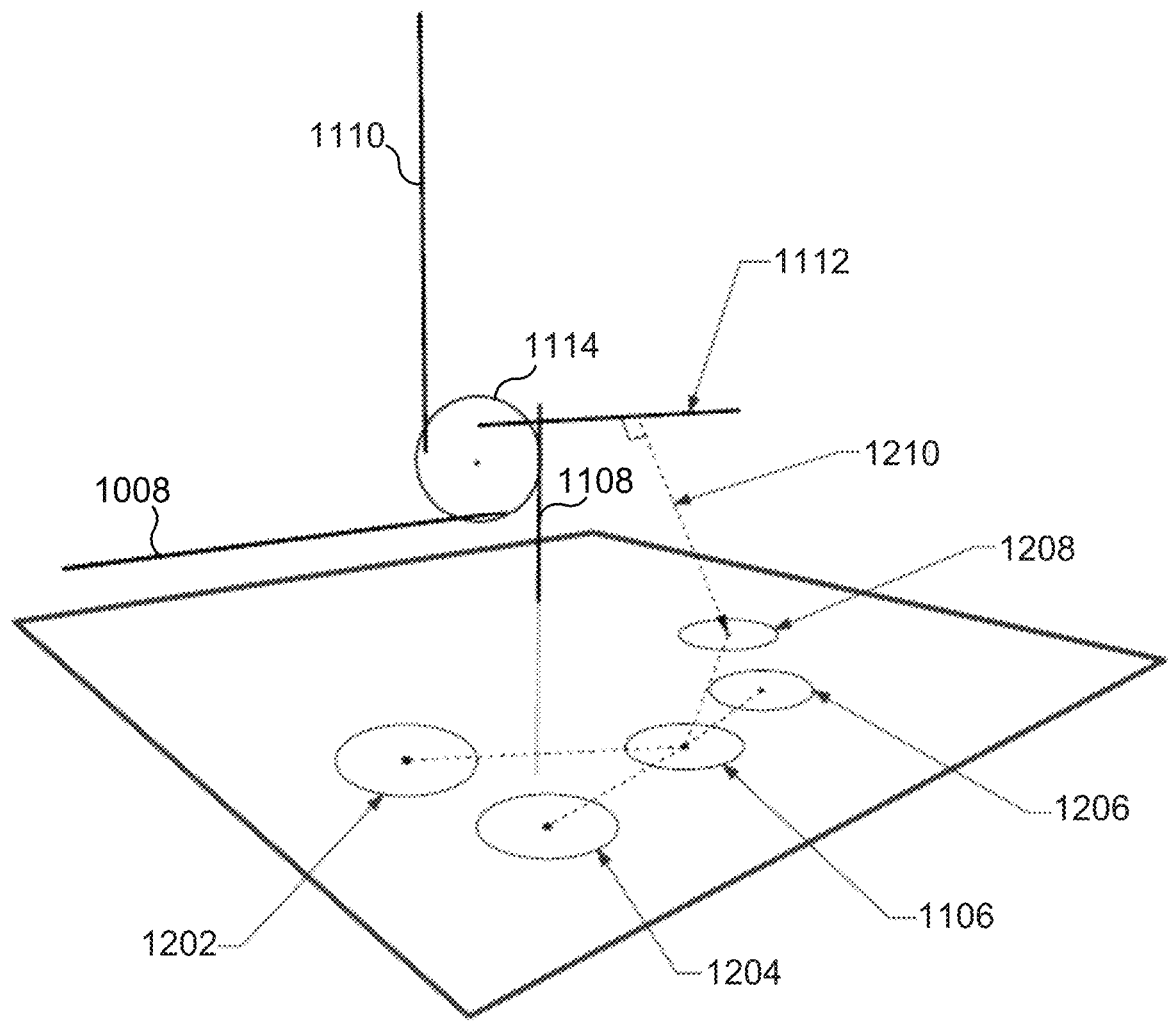
FIG. 12 illustrates couch marker walkout positions at different couch rotation angles and the computation of a tumor beam axis miss distance for a combination of gantry and couch angles according to some aspects.

In some aspects, measuring the couch walkout may include, for each image acquired by an imaging device 416 (e.g., EPID) of the LINAC 100 while the couch 106 rotates and the gantry angle remains fixed, using image processing techniques to find a center of a shadow of the marker 414 in a radiation field of a radiation beam generated using the gantry 102. For example, as shown in FIG. 12, with the gantry 102 at the fixed gantry angle (e.g., 0°), the center of the shadow 1106 of the marker 414 with the couch 106 at a couch angle of 0° and the centers of shadows (e.g., shadows 1202, 1204, 1206, and 1208) of the marker 414 may be found with the couch 106 at different non-zero couch angles.

Some aspects may include using the position of the shadow 1106 of the marker 414 in the radiation field with the couch 106 at the couch angle of 0° as a baseline and compute the movement vector of the shadow of the marker 414 from each image with a non-zero couch rotation. FIG. 12 shows with dotted lines the movement vector from the center of the shadow 1106 of the marker 414 with the couch 106 at the couch angle of 0° to the centers of each of the shadows 1202, 1204, 1206, and 1208 of the marker 414 with the couch 106 at the non-zero couch angles.

Some aspects may include, for different combinations of gantry rotation and couch rotation, computing an error distance between the marker 414 at the couch angle and the three-dimensional beam axis at the gantry angle. For example, as shown in FIG. 12, a marker-to-beam axis distance 1210 between the shadow 1208 of the marker 414 at a particular non-zero couch angle and the three-dimensional beam axis 1112 at a particular non-zero gantry angle may be calculated.

In some aspects, calculating the marker-to-beam axis distance for all combinations of gantry rotation and couch rotation may allow for an understanding of how much the radiation beam will miss the tumor for all combinations of gantry and couch angles (even though the images for couch rotations might have all been acquired with the gantry 106 fixed at one angle).

2.4 Flowcharts

Figure 13:
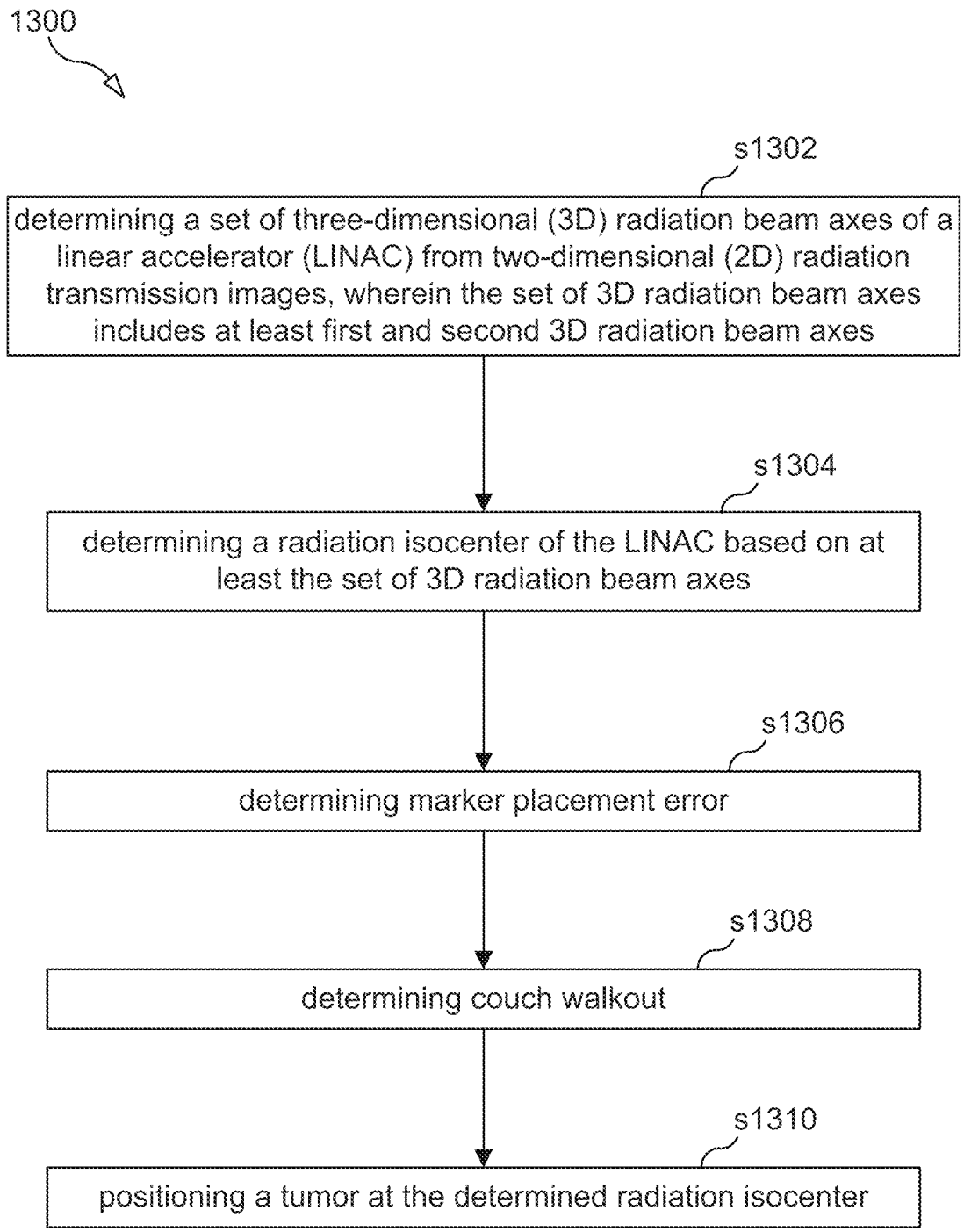
FIG. 13 illustrates a process according to some aspects.

FIG. 13 illustrates a process 1300 according to some aspects. In some aspects, one or more of the steps of the process 1300 may be performed by the LINAC 100 (e.g., a controller of the LINAC 100). In some aspects, one or more of the steps of the process 1300 may be additionally or alternatively be performed by an apparatus (e.g., the apparatus 1900 of FIG. 19). In some aspects, the process 1300 may include a step 1302 of determining a set of three-dimensional (3D) radiation beam axes (e.g., radiation beam axes 1008, 1108, 1112, and 1114). In some aspects, the set of 3D radiation beam axes may include at least first and second 3D radiation beam axes 1008 and 1110. In some aspects, the process 1300 may include a step 1304 of determining a radiation isocenter 1114 based on at least the set of 3D radiation beam axes.

Figure 14:
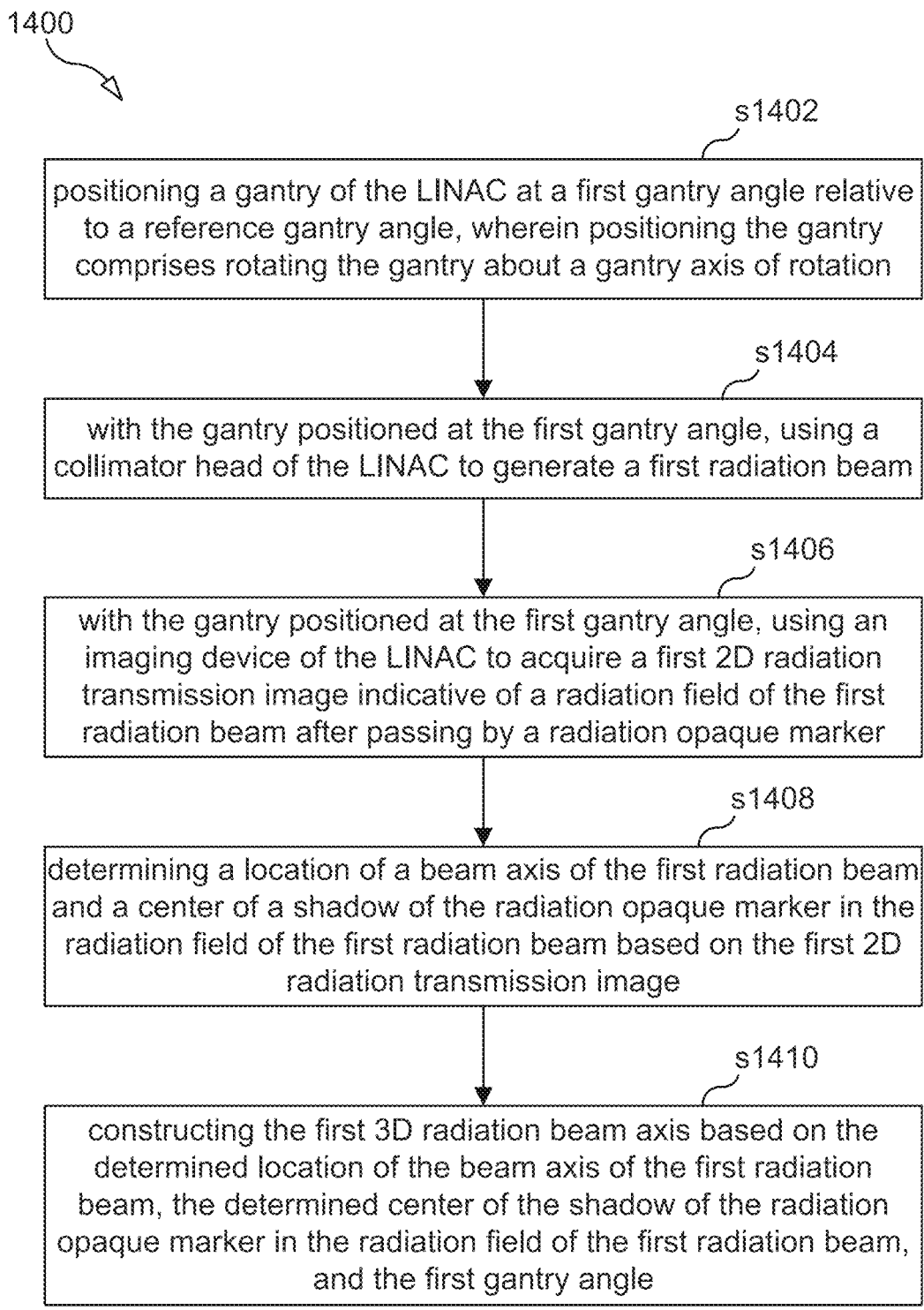
FIG. 14 illustrates a process for determining the first 3D radiation beam axis according to some aspects.

FIG. 14 illustrates a process 1400 for determining the first 3D radiation beam axis 1008 according to some aspects. In some aspects, one or more of the steps of the process 1400 may be performed by the LINAC 100 (e.g., a controller of the LINAC 100). In some aspects, one or more of the steps of the process 1400 may be additionally or alternatively be performed by an apparatus (e.g., the apparatus 1900 of FIG. 19). In some aspects, the process 1400 may be performed in step 1302 of the process 1300 shown in FIG. 13.

In some aspects, the process 1400 may include a step 1402 of positioning a gantry 102 of the LINAC 100 at a first gantry angle (e.g., 90°) relative to a reference gantry angle (e.g., 0°). In some aspects, positioning the gantry 102 may include rotating the gantry 102 about a gantry axis of rotation 208.

In some aspects, the process 1400 may include a step 1404 of, with the gantry 102 positioned at the first gantry angle, using the LINAC 100 to generate a first radiation beam. In some aspects, the process 1400 may include a step 1406, with the gantry 102 positioned at the first gantry angle, using an imaging device 416 of the LINAC 100 to acquire a first two-dimensional (2D) radiation transmission image indicative of a radiation field 902 of the first radiation beam after passing by a radiation opaque marker 414. In some aspects, as shown in FIG. 9, the process 1400 may include a step 1408 of determining a location of the beam axis 908 of the first radiation beam and a center of a shadow 906 of the radiation opaque marker 414 in the radiation field 902 of the first radiation beam based on the first 2D radiation transmission image.

In some aspects, the process 1400 may include a step 1410 of constructing the first 3D radiation beam axis 1008 based on the determined location of the beam axis 908 of the first radiation beam, the determined center of the shadow 906 of the radiation opaque marker 414 in the radiation field 902 of the first radiation beam, and the first gantry angle. In some aspects, as shown in FIG. 10, the step 1410 of constructing the first 3D radiation beam axis 1008 may include rotating the first 2D radiation transmission image about a first image rotation axis that is coincident with the determined center of the shadow 906 of the radiation opaque marker 414 in the radiation field 902 of the first radiation beam and parallel with the gantry axis of rotation 208. In some aspects, the first 2D radiation transmission image may be rotated in an amount equal to the first gantry angle. In some aspects, as shown in FIG. 10, the first 3D radiation beam axis 1008 may be coincident with the determined location of the beam axis of the first radiation beam in the rotated first 2D radiation transmission image and perpendicular to a plane of the rotated 2D first radiation transmission image.

In some alternative aspects, as shown in FIG. 10, the step 1410 of constructing the first 3D radiation beam axis 1008 may include (i) generating an initial 3D radiation beam axis 908 that is coincident with the determined location of the beam axis 908 of the first radiation beam in the first 2D radiation transmission image and perpendicular to a plane of the first 2D radiation transmission image and (ii) rotating the initial 3D radiation beam axis about a first image rotation axis that is coincident with the determined center of the shadow 906 of the radiation opaque marker 414 in the radiation field of the first radiation beam and parallel with the gantry axis of rotation. In some aspects, the initial 3D radiation beam axis may be rotated in an amount equal to the first gantry angle.

In some aspects, determining the second 3D radiation beam axis 1110 (e.g., in step 1302 of the process 1300) may include positioning the gantry 102 of the LINAC 100 at a second gantry angle (e.g., 180°) relative to the reference gantry angle (e.g., 0°). In some aspects, determining the second 3D radiation beam axis 1110 may include, with the gantry 102 positioned at the second gantry angle, using the LINAC 100 to generate a second radiation beam. In some aspects, determining the second 3D radiation beam axis 1110 may include, with the gantry 102 positioned at the second gantry angle, using the imaging device 416 of the LINAC 100 to acquire a second 2D radiation transmission image indicative of a radiation field of the second radiation beam after passing by the radiation opaque marker 414. In some aspects, determining the second 3D radiation beam axis 1110 may include determining a location of a beam axis of the second radiation beam and a center of a shadow of the radiation opaque marker 414 in the radiation field of the second radiation beam based on the second 2D radiation transmission image. In some aspects, determining the second 3D radiation beam axis 1110 may include constructing the second 3D radiation beam axis 1110 based on the determined location of the beam axis of the second radiation beam, the determined center of the shadow of the radiation opaque marker 414 in the radiation field of the second radiation beam, and the second gantry angle.

In some aspects, constructing the second 3D radiation beam axis 1110 (e.g., in step 1302 of the process 1300) may include rotating the second 2D radiation transmission image about a second image rotation axis that is coincident with the determined center of the shadow of the radiation opaque marker 414 in the radiation field of the second radiation beam and parallel with the gantry axis of rotation 208. In some aspects, the second 2D radiation transmission image may be rotated in an amount equal to the second gantry angle. In some aspects, the second 3D radiation beam axis may be coincident with the determined location of the beam axis of the second radiation beam in the rotated second 2D radiation transmission image and perpendicular to a plane of the rotated second 2D radiation transmission image.

In some aspects, constructing the second 3D radiation beam axis 1110 (e.g., in step 1302 of the process 1300) may include (i) generating an initial second 3D radiation beam axis that is coincident with the determined location of the beam axis of the second radiation beam in the second 2D radiation transmission image and perpendicular to a plane of the second 2D radiation transmission image and (ii) rotating the initial second 3D radiation beam axis about a second image rotation axis that is coincident with the determined center of the shadow of the radiation opaque marker in the radiation field of the second radiation beam and parallel with the gantry axis of rotation. In some aspects, the initial second 3D radiation beam axis may be rotated in an amount equal to the second gantry angle.

In some aspects, the couch 106 may be positioned at a fixed couch angle (e.g., 0°) while the LINAC 100 is used to generate the first and second radiation beams and the imaging device of the LINAC is used to acquire the first and second 2D radiation transmission images (e.g., in step 1302 of the process 1300 and/or in at least steps 1402, 1404, and 1406 of the process 1400).

Figure 15:
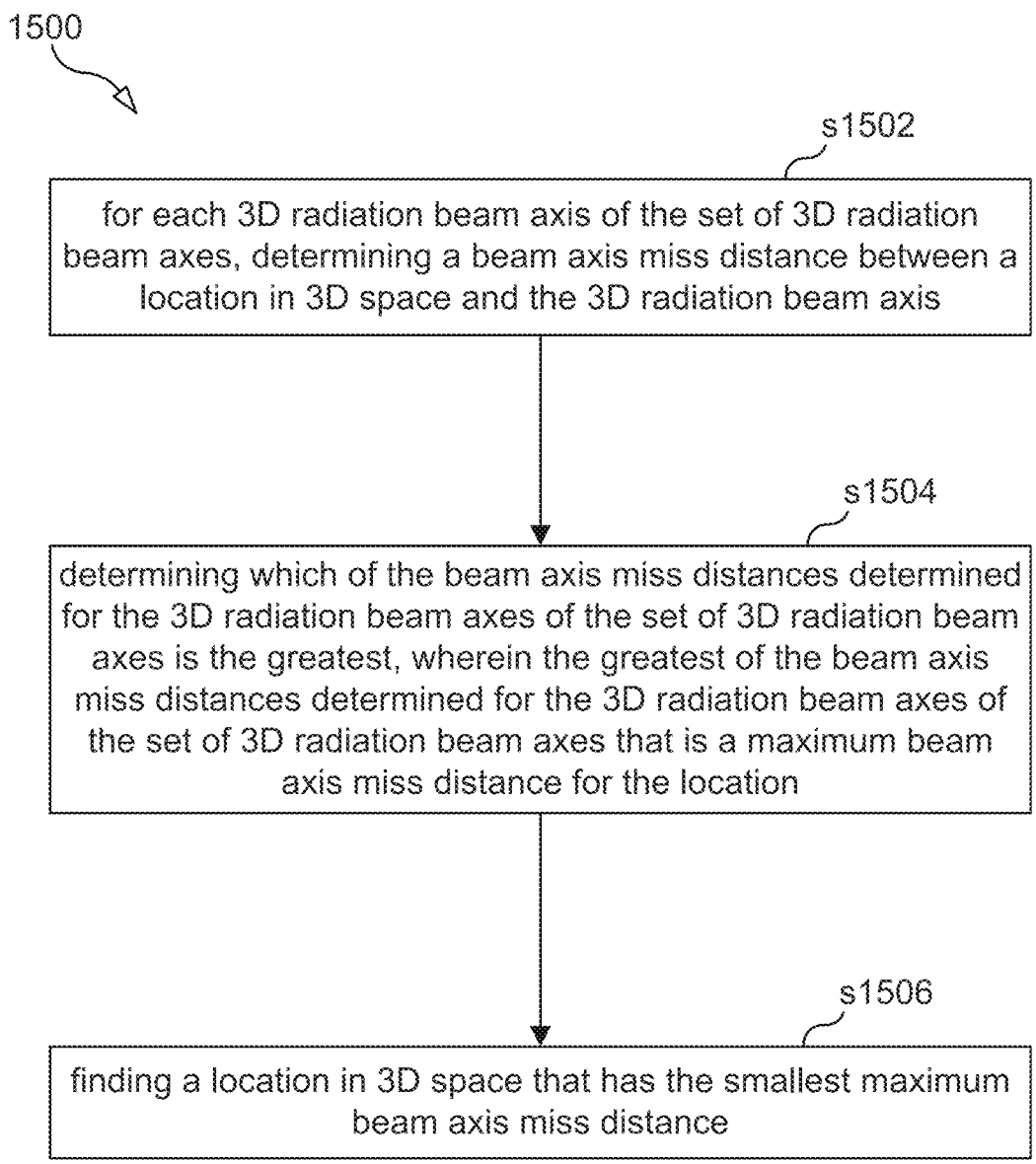
FIG. 15 illustrates a process for determining a radiation isocenter according to some aspects.

FIG. 15 illustrates a process 1500 for determining the radiation isocenter 1114 according to some aspects. In some aspects, one or more of the steps of the process 1500 may be performed by the LINAC 100 (e.g., a controller of the LINAC 100). In some aspects, one or more of the steps of the process 1500 may be additionally or alternatively be performed by an apparatus (e.g., the apparatus 1900 of FIG. 19). In some aspects, the process 1500 may be performed in step 1304 of the process 1300 shown in FIG. 13.

In some aspects, the process 1500 may include a step 1502 of, for each 3D radiation beam axis of the set of 3D radiation beam axes (e.g., including 3D radiation beam axes 1008, 1108, 1112, and 1114), determining a beam axis miss distance between a location in 3D space and the 3D radiation beam axis. In some aspects, the beam axis miss distance between the location in 3D space and the 3D radiation beam axis may be the shortest distance between the location and the 3D radiation beam axis. In some aspects, the process 1500 may include a step 1504 of determining which of the beam axis miss distances determined for the 3D radiation beam axes of the set of 3D radiation beam axes is the greatest. In some aspects, the greatest of the beam axis miss distances determined for the 3D radiation beam axes of the set of 3D radiation beam axes may be a maximum beam axis miss distance for the location. In some aspects, the process 1500 may include a step 1506 of finding a location in 3D space that has the smallest maximum beam axis miss distance. In some aspects, a size of the radiation isocenter 1114 may be the maximum beam axis miss distance for the location. In some alternative aspects, instead of finding the location that minimizes the maximum beam axis distance, other metrics could used (e.g., minimizing the average of the beam axis miss distances, minimizing the root mean squared error of the beam axis miss distances, or combinations thereof).

In some aspects, as shown in FIG. 13, the process 1300 may include an optional step 1306 of determining a marker placement error. Some aspects may include determining the marker placement error as a vector from a center of the shadow of the radiation opaque marker 414 in the radiation field to the determined radiation isocenter 1114. In some aspects, the process 1300 may include using the determined marker placement error to move the radiation opaque marker 414 to the determined radiation isocenter 1114.

In some aspects, as shown in FIG. 13, the process 1300 may include an optional step 1308 of determining couch walkout.

In some aspects, as shown in FIG. 13, the process 1300 may include an optional step 1310 of positioning a tumor at the determined radiation isocenter 1114.

Figure 16:
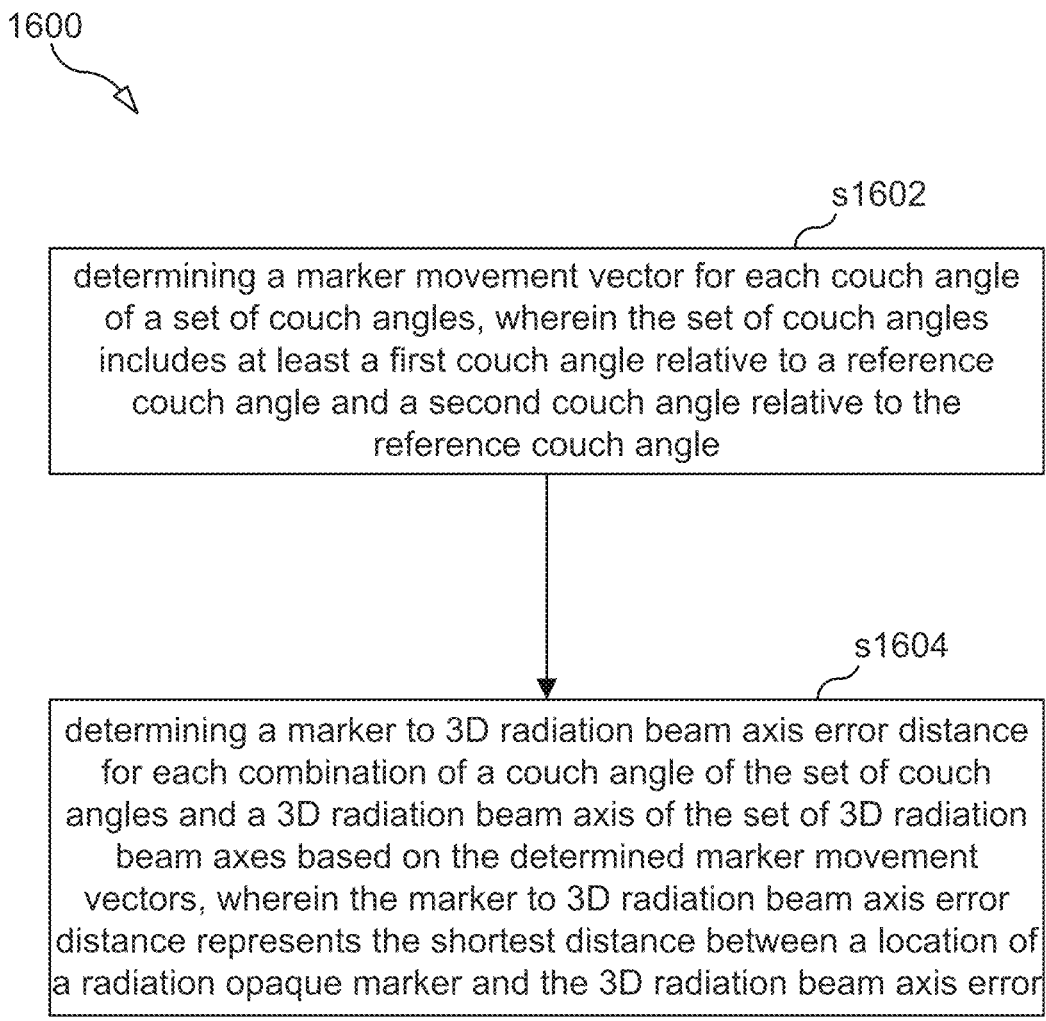
FIG. 16 illustrates a process for determining couch walkout according to some aspects.

FIG. 16 illustrates a process 1600 for determining couch walkout according to some aspects. In some aspects, one or more of the steps of the process 1600 may be performed by the LINAC 100 (e.g., a controller of the LINAC 100). In some aspects, one or more of the steps of the process 1600 may be additionally or alternatively be performed by an apparatus (e.g., the apparatus 1900 of FIG. 19). In some aspects, the process 1600 may be performed in step 1308 of the process 1300 shown in FIG. 13.

In some aspects, the process 1600 may include a step 1602 of determining a marker movement vector for each couch angle of a set of couch angles. In some aspects, the set of couch angles may include at least a first couch angle relative to a reference couch angle (e.g., 0°) and a second couch angle relative to the reference couch angle. In some aspects, the process 1600 may include a step 1604 of determining a marker to 3D radiation beam axis error distance (e.g., marker to 3D radiation beam axis error distance 1210) for each combination of a couch angle of the set of couch angles and a 3D radiation beam axis of the set of 3D radiation beam axes based on the determined marker movement vectors. In some aspects, the marker to 3D radiation beam axis error distance may represent the shortest distance between a location of a radiation opaque marker and the 3D radiation beam axis error.

Figure 17:
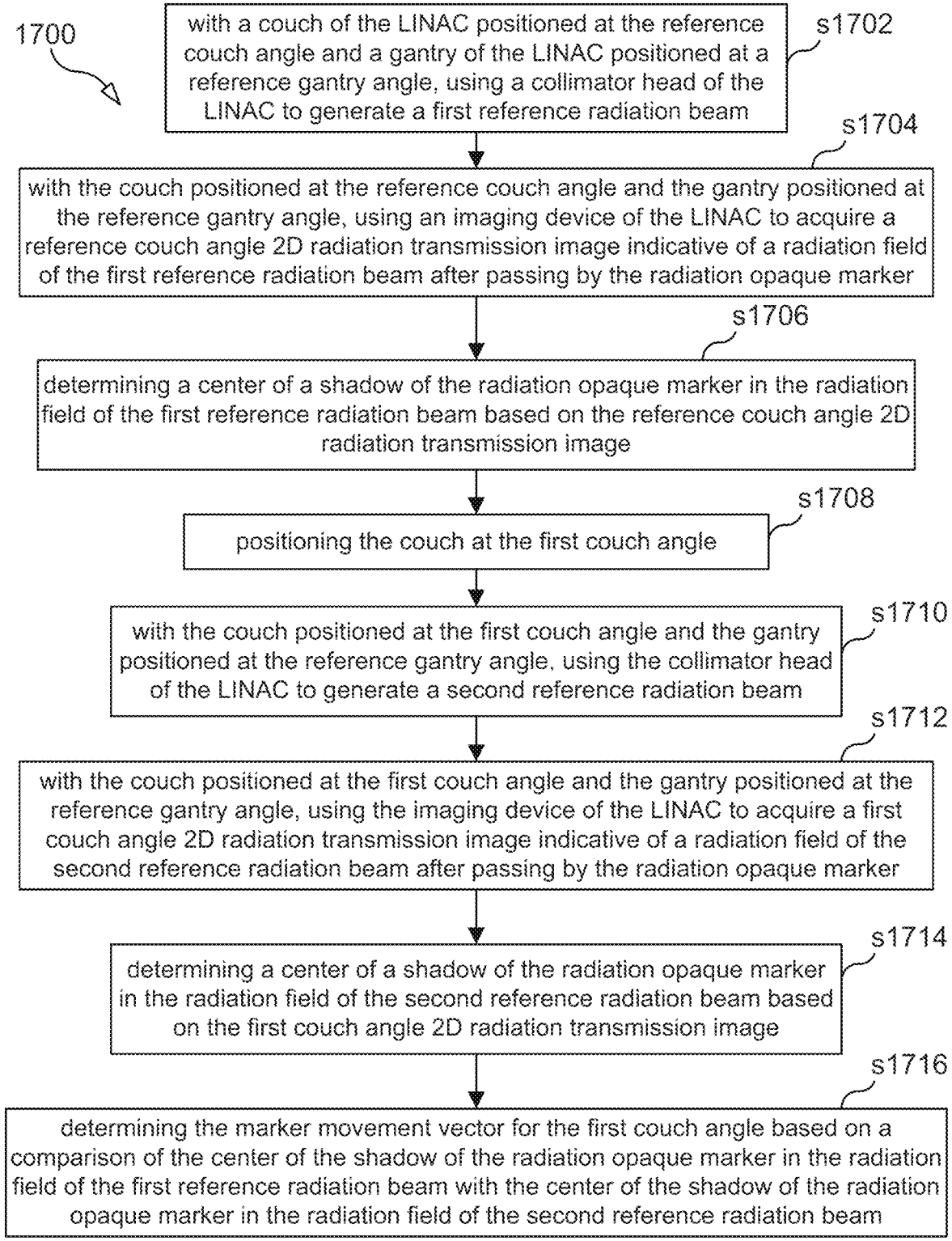
FIG. 17 illustrates a process for determining a marker movement vector for a couch angle according to some aspects.

FIG. 17 illustrates a process 1700 for determining a marker movement vector for a couch angle (e.g., a first couch angle) to some aspects. In some aspects, one or more of the steps of the process 1700 may be performed by the LINAC 100 (e.g., a controller of the LINAC 100). In some aspects, one or more of the steps of the process 1700 may be additionally or alternatively be performed by an apparatus (e.g., the apparatus 1900 of FIG. 19). In some aspects, the process 1700 may be performed in step 1602 of the process 1600 and/or in step 1308 of the process 1300 shown in FIG. 13.

In some aspects, the process 1700 may include a step 1702 of, with a couch 106 of the LINAC 100 positioned at the reference couch angle and a gantry 102 of the LINAC 100 positioned at a reference gantry angle (e.g., 0°), using the LINAC 100 to generate a first reference radiation beam. In some aspects, the process 1700 may include a step 1704 of, with the couch 106 positioned at the reference couch angle and the gantry 102 positioned at the reference gantry angle, using an imaging device 416 of the LINAC 100 to acquire a reference couch angle two-dimensional (2D) radiation transmission image indicative of a radiation field 1102 of the first reference radiation beam after passing by the radiation opaque marker 414. In some aspects, the process 1700 may include a step 1706 of determining a center of a shadow 1106 of the radiation opaque marker 414 in the radiation field 1102 of the first reference radiation beam based on the reference couch angle 2D radiation transmission image.

In some aspects, the process 1700 may include a step 1708 of positioning the couch at the first couch angle. In some aspects, the process 1700 may include a step 1710 of, with the couch 106 positioned at the first couch angle and the gantry 102 positioned at the reference gantry angle, using the LINAC 100 to generate a second reference radiation beam. In some aspects, the process 1700 may include a step 1712 of, with the couch 106 positioned at the first couch angle and the gantry 102 positioned at the reference gantry angle, using the imaging device 416 of the LINAC 100 to acquire a first couch angle 2D radiation transmission image indicative of a radiation field of the second reference radiation beam after passing by the radiation opaque marker. In some aspects, the process 1700 may include a step 1714 of determining a center of a shadow 1208 of the radiation opaque marker 414 in the radiation field of the second reference radiation beam based on the first couch angle 2D radiation transmission image. In some aspects, the process 1700 may include a step 1716 of determining the marker movement vector for the first couch angle based on a comparison of the center of the shadow 1106 of the radiation opaque marker 414 in the radiation field 1102 of the first reference radiation beam with the center of the shadow 1208 of the radiation opaque marker in the radiation field of the second reference radiation beam.

In some aspects, determining the marker movement vector for the second couch angle in step 1602 may include positioning the couch 106 at the second couch angle. In some aspects, determining the marker movement vector for the second couch angle in step 1602 may include, with the couch 106 positioned at the second couch angle and the gantry 102 positioned at the reference gantry angle, using the LINAC 100 to generate a third reference radiation beam. In some aspects, determining the marker movement vector for the second couch angle in step 1602 may include, with the couch 106 positioned at the second couch angle and the gantry 102 positioned at the reference gantry angle, using the imaging device 416 of the LINAC 100 to acquire a second couch angle 2D radiation transmission image indicative of a radiation field of the third reference radiation beam after passing by the radiation opaque marker 414. In some aspects, determining the marker movement vector for the second couch angle in step 1602 may include determining a center of a shadow 1206 of the radiation opaque marker 414 in the radiation field of the third reference radiation beam based on the second couch angle 2D radiation transmission image. In some aspects, determining the marker movement vector for the second couch angle in step 1602 may include determining the marker movement vector for the second couch angle based on a comparison of the center of the shadow 1106 of the radiation opaque marker 414 in the radiation field 1102 of the first reference radiation beam with the center of the shadow 1206 of the radiation opaque marker in the radiation field of the third reference radiation beam.

In some aspects, the process 1600 may further include determining a clinical isocenter. In some aspects, determining the clinical isocenter may include determining a location in space that minimizes a maximum marker to beam axis error distance. In some aspects, determining the location in space that minimizes the maximum marker to 3D radiation beam axis error distance may include predicting a couch axis of rotation based on shadows of the radiation opaque marker at different couch angles. In some aspects, determining the location in space that minimizes the maximum marker to 3D radiation beam axis error distance may include predicting a set of positions of the radiation opaque marker 414 at a new reference position displaced by couch rotation about the predicted couch axis of rotation. In some aspects, determining the location in space that minimizes the maximum marker to beam axis error distance may include determining a predicted marker to 3D radiation beam axis error distance for each combination of a couch angle of the set of couch angles and a 3D radiation beam axis of the set of 3D radiation beam axes based on the determined marker movement vectors, and the predicted marker to 3D radiation beam axis error distance may represent the shortest distance between a location of a radiation opaque marker and the 3D radiation beam axis error. In some aspects, determining the location in space that minimizes the maximum marker to beam axis error distance may include determining a reference marker position that minimizes the maximum marker to beam axis error distance. In some aspects, the process 1600 may further include a step of placing a tumor at the determined clinical isocenter.

2.5 LINAC Controller

Figure 18:
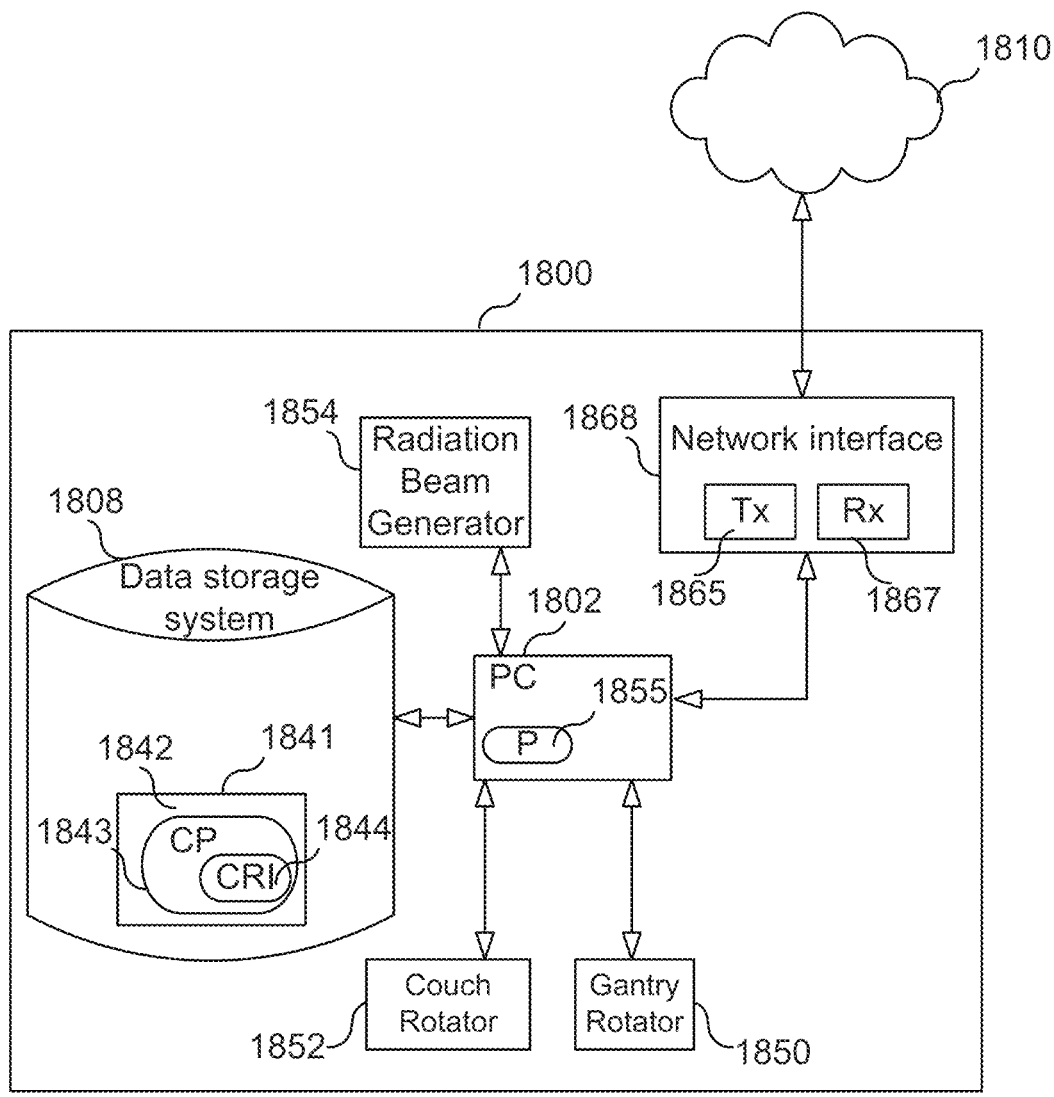
FIG. 18 illustrates a controller of a LINAC according to some aspects.

FIG. 18 is a block diagram of a controller 1800 of a LINAC 100 according to some aspects. As shown in FIG. 18, the controller 1800 may comprise: processing circuitry (PC) 1802, which may include one or more processors (P) 1855 (e.g., one or more general purpose microprocessors and/or one or more other processors, such as an application specific integrated circuit (ASIC), field-programmable gate arrays (FPGAs), and the like), which processors may be co-located in a single housing or in a single data center or may be geographically distributed (i.e., the system may be a distributed computing apparatus); a network interface 1868 comprising a transmitter (Tx) 1865 and a receiver (Rx) 1867 for enabling the controller 1800 to transmit data to and receive data from other nodes connected to a network 1810 (e.g., an Internet Protocol (IP) network) to which network interface 1868 is connected; a gantry rotator 1850 configured to rotate the gantry 102 about the gantry axis of rotation 208; a couch rotator 1852 configured to rotate the couch 106 about the couch axis of rotation 310; a radiation beam generator 1854 configured to generate an electron beam in a waveguide of the LINAC 100; and a local storage unit (a.k.a., "data storage system") 1808, which may include one or more non-volatile storage devices and/or one or more volatile storage devices. In aspects where PC 1802 includes a programmable processor, a computer program product (CPP) 1841 may be provided. In some aspects, the CPP 1841 may include a computer readable medium (CRM) 1842 storing a computer program (CP) 1843 comprising computer readable instructions (CRI) 1844. In some aspects, the CRM 1842 may be a non-transitory computer readable medium, such as, magnetic media (e.g., a hard disk), optical media, memory devices (e.g., random access memory, flash memory), and the like. In some aspects, the CRI 1844 of computer program 1843 may be configured such that when executed by PC 1802, the CRI causes the LINAC 100 to perform steps described herein (e.g., one or more steps described herein with reference to the flowcharts herein). In other aspects, the controller 1800 may be configured to perform steps described herein without the need for code. That is, for example, the PC 1802 may consist merely of one or more ASICs. Hence, the features of the aspects described herein may be implemented in hardware and/or software.

2.6 Apparatus

Figure 19:
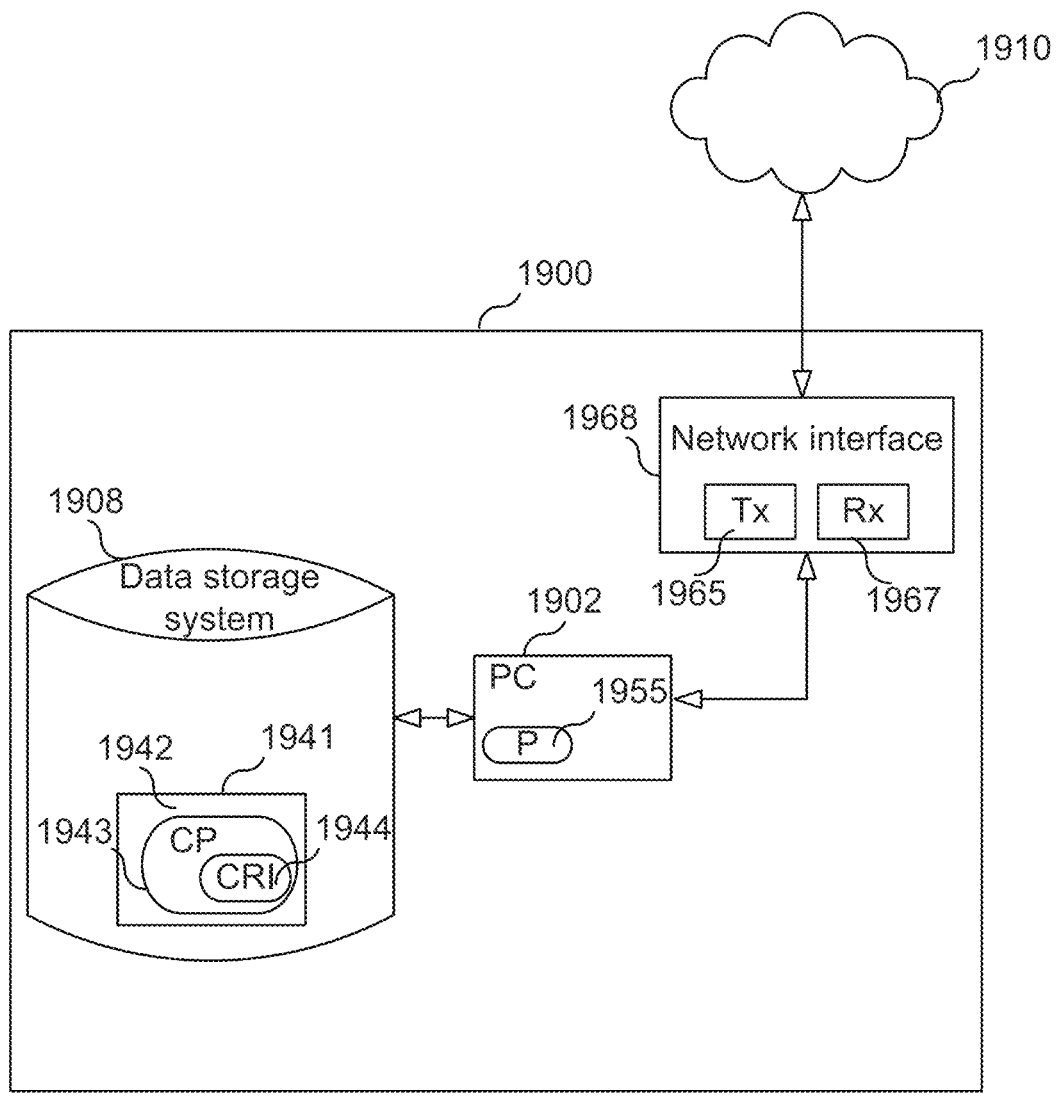
FIG. 19 illustrates an apparatus according to some aspects.

FIG. 19 is a block diagram of an apparatus 1900 according to some aspects. As shown in FIG. 19, the apparatus 1900 may comprise: processing circuitry (PC) 1902, which may include one or more processors (P) 1955 (e.g., one or more general purpose microprocessors and/or one or more other processors, such as an application specific integrated circuit (ASIC), field-programmable gate arrays (FPGAs), and the like), which processors may be co-located in a single housing or in a single data center or may be geographically distributed (i.e., the system may be a distributed computing apparatus); a network interface 1968 comprising a transmitter (Tx) 1965 and a receiver (Rx) 1967 for enabling the apparatus 1900 to transmit data to and receive data from other nodes connected to a network 1910 (e.g., an Internet Protocol (IP) network) to which network interface 1968 is connected; and a local storage unit (a.k.a., "data storage system") 1908, which may include one or more non-volatile storage devices and/or one or more volatile storage devices. In aspects where PC 1902 includes a programmable processor, a computer program product (CPP) 1941 may be provided. In some aspects, the CPP 1941 may include a computer readable medium (CRM) 1942 storing a computer program (CP) 1943 comprising computer readable instructions (CRI) 1944. In some aspects, the CRM 1942 may be a non-transitory computer readable medium, such as, magnetic media (e.g., a hard disk), optical media, memory devices (e.g., random access memory, flash memory), and the like. In some aspects, the CRI 1944 of computer program 1943 may be configured such that when executed by PC 1902, the CRI causes the apparatus 1900 to perform steps described herein (e.g., one or more steps described herein with reference to the flowcharts herein). In other aspects, the apparatus 1900 may be configured to perform steps described herein without the need for code. That is, for example, the PC 1902 may consist merely of one or more ASICs. Hence, the features of the aspects described herein may be implemented in hardware and/or software.

While various embodiments are described herein, it should be understood that they have been presented by way of example only, and not limitation. Thus, the breadth and scope of this disclosure should not be limited by any of the above-described exemplary embodiments. Moreover, any combination of the above-described elements in all possible variations thereof is encompassed by the disclosure unless otherwise indicated herein or otherwise clearly contradicted by context.

Additionally, while the processes described above and illustrated in the drawings are shown as a sequence of steps, this was done solely for the sake of illustration. Accordingly, it is contemplated that some steps may be added, some steps may be omitted, the order of the steps may be re-arranged, and some steps may be performed in parallel.

What is claimed is:

1. A method comprising:
   determining a set of three-dimensional (3D) radiation beam axes of a linear accelerator (LINAC) from two-dimensional (2D) radiation transmission images, wherein the set of 3D radiation beam axes includes at least first and second 3D radiation beam axes; and
   determining a radiation isocenter of the LINAC based on at least the set of 3D radiation beam axes;
   wherein determining the first 3D radiation beam axis comprises:
      positioning a gantry of the LINAC at a first gantry angle relative to a reference gantry angle, wherein positioning the gantry comprises rotating the gantry about a gantry axis of rotation;
      with the gantry positioned at the first gantry angle, using the LINAC to generate a first radiation beam;
      with the gantry positioned at the first gantry angle, using an imaging device of the LINAC to acquire a first two-dimensional (2D) radiation transmission image indicative of a radiation field of the first radiation beam after passing by a radiation opaque marker;
      determining a location of a beam axis of the first radiation beam and a center of a shadow of the radiation opaque marker in the radiation field of the first radiation beam based on the first 2D radiation transmission image; and
      constructing the first 3D radiation beam axis based on the determined location of the beam axis of the first radiation beam, the determined center of the shadow of the radiation opaque marker in the radiation field of the first radiation beam, and the first gantry angle;
   wherein determining the second 3D radiation beam axis comprises:
      positioning the gantry of the LINAC at a second gantry angle relative to the reference gantry angle;

with the gantry positioned at the second gantry angle, using the LINAC to generate a second radiation beam;

with the gantry positioned at the second gantry angle, using the imaging device of the LINAC to acquire a second 2D radiation transmission image indicative of a radiation field of the second radiation beam after passing by the radiation opaque marker;

determining a location of a beam axis of the second radiation beam and a center of a shadow of the radiation opaque marker in the radiation field of the second radiation beam based on the second 2D radiation transmission image; and constructing the second 3D radiation beam axis based on the determined location of the beam axis of the second radiation beam, the determined center of the shadow of the radiation opaque marker in the radiation field of the second radiation beam, and the second gantry angle.

2. The method of claim 1, wherein:

constructing the first 3D radiation beam axis comprises rotating the first 2D radiation transmission image about a first image rotation axis that is coincident with the determined center of the shadow of the radiation opaque marker in the radiation field of the first radiation beam and parallel with the gantry axis of rotation;

the first 2D radiation transmission image is rotated in an amount equal to the first gantry angle; and the first 3D radiation beam axis is coincident with the determined location of the beam axis of the first radiation beam in the rotated first 2D radiation transmission image and perpendicular to a plane of the rotated first 2D radiation transmission image.

3. The method of claim 1, wherein constructing the first 3D radiation beam axis comprises:

generating an initial 3D radiation beam axis that is coincident with the determined location of the beam axis of the first radiation beam in the first 2D radiation transmission image and perpendicular to a plane of the first 2D radiation transmission image; and rotating the initial 3D radiation beam axis about a first image rotation axis that is coincident with the determined center of the shadow of the radiation opaque marker in the radiation field of the first radiation beam and parallel with the gantry axis of rotation;

wherein the initial 3D radiation beam axis is rotated in an amount equal to the first gantry angle.

4. The method of claim 1, wherein:

constructing the second 3D radiation beam axis comprises rotating the second 2D radiation transmission image about a second image rotation axis that is coincident with the determined center of the shadow of the radiation opaque marker in the radiation field of the second radiation beam and parallel with the gantry axis of rotation;

the second 2D radiation transmission image is rotated in an amount equal to the second gantry angle; and the second 3D radiation beam axis is coincident with the determined location of the beam axis of the second radiation beam in the rotated second 2D radiation transmission image and perpendicular to a plane of the rotated second 2D radiation transmission image.

5. The method of claim 1, wherein constructing the second 3D radiation beam axis comprises:

generating an initial second 3D radiation beam axis that is coincident with the determined location of the beam axis of the second radiation beam in the second 2D radiation transmission image and perpendicular to a plane of the second 2D radiation transmission image; and rotating the initial second 3D radiation beam axis about a second image rotation axis that is coincident with the determined center of the shadow of the radiation opaque marker in the radiation field of the second radiation beam and parallel with the gantry axis of rotation;

wherein the initial second 3D radiation beam axis is rotated in an amount equal to the second gantry angle.

6. The method of claim 1, wherein a couch is positioned at a fixed couch angle while the LINAC is used to generate the first and second radiation beams and the imaging device of the LINAC is used to acquire the first and second 2D radiation transmission images.

7. The method of claim 1, wherein determining the radiation isocenter comprises:

for each 3D radiation beam axis of the set of 3D radiation beam axes, determining a beam axis miss distance between a location in 3D space and the 3D radiation beam axis;

determining which of the beam axis miss distances determined for the 3D radiation beam axes of the set of 3D radiation beam axes is the greatest, wherein the greatest of the beam axis miss distances determined for the 3D radiation beam axes of the set of 3D radiation beam axes is a maximum beam axis miss distance for the location; and finding a location in 3D space that has the smallest maximum beam axis miss distance.

8. The method of claim 7, wherein a size of the radiation isocenter is the maximum beam axis miss distance for the location.

9. The method of claim 1, further comprising positioning a tumor at the determined radiation isocenter.

10. The method of claim 1, further comprising:

determining a marker movement vector for each couch angle of a set of couch angles, wherein the set of couch angles includes at least a first couch angle relative to a reference couch angle and a second couch angle relative to the reference couch angle; and determining a marker to 3D radiation beam axis error distance for each combination of a couch angle of the set of couch angles and a 3D radiation beam axis of the set of 3D radiation beam axes based on the determined marker movement vectors, wherein the marker to 3D radiation beam axis error distance represents the shortest distance between a location of a radiation opaque marker and the 3D radiation beam axis.

11. The method of claim 10, wherein determining the marker movement vector for the first couch angle comprises:

with a couch of the LINAC positioned at the reference couch angle and a gantry of the LINAC positioned at a reference gantry angle, using the LINAC to generate a first reference radiation beam;

with the couch positioned at the reference couch angle and the gantry positioned at the reference gantry angle, using an imaging device of the LINAC to acquire a reference couch angle two-dimensional (2D) radiation transmission image indicative of a radiation field of the first reference radiation beam after passing by the radiation opaque marker;

determining a center of a shadow of the radiation opaque marker in the radiation field of the first reference radiation beam based on the reference couch angle 2D radiation transmission image;
positioning the couch at the first couch angle;
with the couch positioned at the first couch angle and the gantry positioned at the reference gantry angle, using the LINAC to generate a second reference radiation beam;
with the couch positioned at the first couch angle and the gantry positioned at the reference gantry angle, using the imaging device of the LINAC to acquire a first couch angle 2D radiation transmission image indicative of a radiation field of the second reference radiation beam after passing by the radiation opaque marker;
determining a center of a shadow of the radiation opaque marker in the radiation field of the second reference radiation beam based on the first couch angle 2D radiation transmission image; and
determining the marker movement vector for the first couch angle based on a comparison of the center of the shadow of the radiation opaque marker in the radiation field of the first reference radiation beam with the center of the shadow of the radiation opaque marker in the radiation field of the second reference radiation beam.

12. The method of claim 11, wherein determining the marker movement vector for the second couch angle comprises:
positioning the couch at the second couch angle;
with the couch positioned at the second couch angle and the gantry positioned at the reference gantry angle, using the LINAC to generate a third reference radiation beam;
with the couch positioned at the second couch angle and the gantry positioned at the reference gantry angle, using the imaging device of the LINAC to acquire a second couch angle 2D radiation transmission image indicative of a radiation field of the third reference radiation beam after passing by the radiation opaque marker;
determining a center of a shadow of the radiation opaque marker in the radiation field of the third reference radiation beam based on the second couch angle 2D radiation transmission image; and
determining the marker movement vector for the second couch angle based on a comparison of the center of the shadow of the radiation opaque marker in the radiation field of the first reference radiation beam with the center of the shadow of the radiation opaque marker in the radiation field of the third reference radiation beam.

13. The method of claim 10, further comprising determining a clinical isocenter, wherein determining the clinical isocenter comprises determining a location in space that minimizes a maximum marker to 3D radiation beam axis error distance.

14. The method of claim 13, wherein determining the location in space that minimizes the maximum marker to 3D radiation beam axis error distance comprises:
predicting a couch axis of rotation based on shadows of the radiation opaque marker at different couch angles;
predicting a set of positions of the radiation opaque marker at a new reference position displaced by couch rotation about the predicted couch axis of rotation;
determining a predicted marker to 3D radiation beam axis error distance for each combination of a couch angle of the set of couch angles and a 3D radiation beam axis of the set of 3D radiation beam axes based on the determined marker movement vectors, wherein the predicted marker to 3D radiation beam axis error distance represents the shortest distance between a location of a radiation opaque marker and the 3D radiation beam axis; and
determining a reference marker position that minimizes the maximum marker to beam axis error distance.

15. The method of claim 13, further comprising placing a tumor at the determined clinical isocenter.

16. An apparatus configured to:
determine a set of three-dimensional (3D) radiation beam axes of a linear accelerator (LINAC) from two-dimensional (2D) radiation transmission images, wherein the set of 3D radiation beam axes includes at least first and second 3D radiation beam axes; and
determine a radiation isocenter of the LINAC based on at least the set of 3D radiation beam axes;
wherein, in determining the first 3D radiation beam axis, the apparatus is configured to:
position a gantry of the LINAC at a first gantry angle relative to a reference gantry angle, wherein positioning the gantry comprises rotating the gantry about a gantry axis of rotation;
with the gantry positioned at the first gantry angle, use the LINAC to generate a first radiation beam;
with the gantry positioned at the first gantry angle, use an imaging device of the LINAC to acquire a first two-dimensional (2D) radiation transmission image indicative of a radiation field of the first radiation beam after passing by a radiation opaque marker;
determine a location of a beam axis of the first radiation beam and a center of a shadow of the radiation opaque marker in the radiation field of the first radiation beam based on the first 2D radiation transmission image; and
construct the first 3D radiation beam axis based on the determined location of the beam axis of the first radiation beam, the determined center of the shadow of the radiation opaque marker in the radiation field of the first radiation beam, and the first gantry angle;
wherein, in determining the second 3D radiation beam axis, the apparatus is configured to:
position the gantry of the LINAC at a second gantry angle relative to the reference gantry angle;
with the gantry positioned at the second gantry angle, use the LINAC to generate a second radiation beam;
with the gantry positioned at the second gantry angle, use the imaging device of the LINAC to acquire a second 2D radiation transmission image indicative of a radiation field of the second radiation beam after passing by the radiation opaque marker;
determine a location of a beam axis of the second radiation beam and a center of a shadow of the radiation opaque marker in the radiation field of the second radiation beam based on the second 2D radiation transmission image; and
construct the second 3D radiation beam axis based on the determined location of the beam axis of the second radiation beam, the determined center of the shadow of the radiation opaque marker in the radiation field of the second radiation beam, and the second gantry angle.

17. A method comprising:
determining a marker movement vector for each couch angle of a set of couch angles of a linear accelerator (LINAC), wherein the set of couch angles includes at least a first couch angle relative to a reference couch angle and a second couch angle relative to the reference couch angle; and determining a marker to 3D radiation beam axis error distance for each combination of a couch angle of the set of couch angles and a 3D radiation beam axis of a set of 3D radiation beam axes based on the determined marker movement vectors, wherein the marker to 3D radiation beam axis error distance represents the shortest distance between a location of a radiation opaque marker and the 3D radiation beam axis.

18. The method of claim 17, further comprising placing a tumor at a location determined based on the determined marker to 3D radiation beam axis error distance for each combination of a couch angle of the set of couch angles and a 3D radiation beam axis of a set of 3D radiation beam axes.

19. The method of claim 17, wherein a marker assembly includes the radiation opaque marker, and a base of the marker assembly is set on the couch.

20. The method of claim 17, wherein determining the marker movement vector for the first couch angle comprises:

with a couch of the LINAC positioned at the reference couch angle and a gantry of the LINAC positioned at a reference gantry angle, using the LINAC to generate a first reference radiation beam;

with the couch positioned at the reference couch angle and the gantry positioned at the reference gantry angle, using an imaging device of the LINAC to acquire a reference couch angle two-dimensional (2D) radiation transmission image indicative of a radiation field of the first reference radiation beam after passing by the radiation opaque marker;

determining a center of a shadow of the radiation opaque marker in the radiation field of the first reference radiation beam based on the reference couch angle 2D radiation transmission image;

positioning the couch at the first couch angle;

with the couch positioned at the first couch angle and the gantry positioned at the reference gantry angle, using the LINAC to generate a second reference radiation beam;

with the couch positioned at the first couch angle and the gantry positioned at the reference gantry angle, using the imaging device of the LINAC to acquire a first couch angle 2D radiation transmission image indicative of a radiation field of the second reference radiation beam after passing by the radiation opaque marker;

determining a center of a shadow of the radiation opaque marker in the radiation field of the second reference radiation beam based on the first couch angle 2D radiation transmission image; and determining the marker movement vector for the first couch angle based on a comparison of the center of the shadow of the radiation opaque marker in the radiation field of the first reference radiation beam with the center of the shadow of the radiation opaque marker in the radiation field of the second reference radiation beam; and wherein determining the marker movement vector for the second couch angle comprises:

positioning the couch at the second couch angle;

with the couch positioned at the second couch angle and the gantry positioned at the reference gantry angle, using the LINAC to generate a third reference radiation beam;

with the couch positioned at the second couch angle and the gantry positioned at the reference gantry angle, using the imaging device of the LINAC to acquire a second couch angle 2D radiation transmission image indicative of a radiation field of the third reference radiation beam after passing by the radiation opaque marker;

determining a center of a shadow of the radiation opaque marker in the radiation field of the third reference radiation beam based on the second couch angle 2D radiation transmission image; and determining the marker movement vector for the second couch angle based on a comparison of the center of the shadow of the radiation opaque marker in the radiation field of the first reference radiation beam with the center of the shadow of the radiation opaque marker in the radiation field of the third reference radiation beam.

21. The method of claim 17, wherein the set of 3D radiation beam axes includes at least first and second 3D radiation beam axes;

wherein the first 3D radiation beam was constructed based on a location of a beam axis of a first radiation beam generated with a gantry of the LINAC positioned at a first gantry angle relative to a reference gantry angle, a center of a shadow of the radiation opaque marker in a radiation field of the first radiation beam, and the first gantry angle; and wherein the second 3D radiation beam was constructed based on a location of a beam axis of a second radiation beam generated with the gantry positioned at a second gantry angle relative to the reference gantry angle, a center of a shadow of the radiation opaque marker in a radiation field of the second radiation beam, and the second gantry angle.

22. The method of claim 17, further comprising determining a clinical isocenter, wherein determining the clinical isocenter comprises determining a location in space that minimizes a maximum marker to 3D radiation beam axis error distance.

23. The method of claim 22, wherein determining the location in space that minimizes the maximum marker to 3D radiation beam axis error distance comprises:

predicting a couch axis of rotation based on shadows of the radiation opaque marker at different couch angles;

predicting a set of positions of the radiation opaque marker at a new reference position displaced by couch rotation about the predicted couch axis of rotation;

determining a predicted marker to 3D radiation beam axis error distance for each combination of a couch angle of the set of couch angles and a 3D radiation beam axis of the set of 3D radiation beam axes based on the determined marker movement vectors, wherein the predicted marker to 3D radiation beam axis error distance represents the shortest distance between a location of a radiation opaque marker and the 3D radiation beam axis; and determining a reference marker position that minimizes the maximum marker to beam axis error distance.

24. The method of claim 22, further comprising placing a tumor at the determined clinical isocenter.

25. An apparatus configured to:

determine a marker movement vector for each couch angle of a set of couch angles of a linear accelerator (LINAC) (100), wherein the set of couch angles includes at least a first couch angle relative to a reference couch angle and a second couch angle relative to the reference couch angle; and determine a marker to three-dimensional (3D) radiation beam axis error distance for each combination of a couch angle of the set of couch angles and a 3D radiation beam axis of a set of 3D radiation beam axes based on the determined marker movement vectors, wherein the marker to 3D radiation beam axis error distance represents the shortest distance between a location of a radiation opaque marker and the 3D radiation beam axis.

26. The apparatus of claim 25, wherein the apparatus is configured to, in determining the marker movement vector for the first couch angle:
   with a couch of the LINAC positioned at the reference couch angle and a gantry of the LINAC positioned at a reference gantry angle, use the LINAC to generate a first reference radiation beam;
   with the couch positioned at the reference couch angle and the gantry positioned at the reference gantry angle, use an imaging device of the LINAC to acquire a reference couch angle two-dimensional (2D) radiation transmission image indicative of a radiation field of the first reference radiation beam after passing by the radiation opaque marker;
   determine a center of a shadow of the radiation opaque marker in the radiation field of the first reference radiation beam based on the reference couch angle 2D radiation transmission image;
   position the couch at the first couch angle;
   with the couch positioned at the first couch angle and the gantry positioned at the reference gantry angle, use the LINAC to generate a second reference radiation beam;
   with the couch positioned at the first couch angle and the gantry positioned at the reference gantry angle, use the imaging device of the LINAC to acquire a first couch angle 2D radiation transmission image indicative of a radiation field of the second reference radiation beam after passing by the radiation opaque marker;
   determine a center of a shadow of the radiation opaque marker in the radiation field of the second reference radiation beam based on the first couch angle 2D radiation transmission image; and
   determine the marker movement vector for the first couch angle based on a comparison of the center of the shadow of the radiation opaque marker in the radiation field of the first reference radiation beam with the center of the shadow of the radiation opaque marker in the radiation field of the second reference radiation beam;
wherein the apparatus is configured to, in determining the marker movement vector for the second couch angle:
   position the couch at the second couch angle;
   with the couch positioned at the second couch angle and the gantry positioned at the reference gantry angle, use the LINAC to generate a third reference radiation beam;
   with the couch positioned at the second couch angle and the gantry positioned at the reference gantry angle, use the imaging device of the LINAC to acquire a second couch angle 2D radiation transmission image indicative of a radiation field of the third reference radiation beam after passing by the radiation opaque marker;
   determine a center of a shadow of the radiation opaque marker in the radiation field of the third reference radiation beam based on the second couch angle 2D radiation transmission image; and
   determine the marker movement vector for the second couch angle based on a comparison of the center of the shadow of the radiation opaque marker in the radiation field of the first reference radiation beam with the center of the shadow of the radiation opaque marker in the radiation field of the third reference radiation beam.

27. The apparatus of claim 25, wherein a marker assembly includes the radiation opaque marker, and a base of the marker assembly is set on the couch.

28. The apparatus of claim 25, wherein the set of 3D radiation beam axes includes at least first and second 3D radiation beam axes;
   wherein the first 3D radiation beam was constructed based on a location of a beam axis of a first radiation beam generated with a gantry of the LINAC positioned at a first gantry angle relative to a reference gantry angle, a center of a shadow of the radiation opaque marker in a radiation field of the first radiation beam, and the first gantry angle; and
   wherein the second 3D radiation beam was constructed based on a location of a beam axis of a second radiation beam generated with the gantry positioned at a second gantry angle relative to the reference gantry angle, a center of a shadow of the radiation opaque marker in a radiation field of the second radiation beam, and the second gantry angle.

29. The apparatus of claim 25, wherein the set of 3D radiation beam axes includes at least first and second 3D radiation beam axes;
   wherein the first 3D radiation beam was constructed based on a location of a beam axis of a first radiation beam generated with a gantry of the LINAC positioned at a first gantry angle relative to a reference gantry angle, a center of a shadow of the radiation opaque marker in a radiation field of the first radiation beam, and the first gantry angle; and
   wherein the second 3D radiation beam was constructed based on a location of a beam axis of a second radiation beam generated with the gantry positioned at a second gantry angle relative to the reference gantry angle, a center of a shadow of the radiation opaque marker in a radiation field of the second radiation beam, and the second gantry angle.

30. The apparatus of claim 25, wherein the apparatus is further configured to determine a clinical isocenter, and the apparatus is configured to, in determining the clinical isocenter, determine a location in space that minimizes a maximum marker to 3D radiation beam axis error distance.

* * * * *